US008353859B2

(12) United States Patent
Derichs

(10) Patent No.: US 8,353,859 B2
(45) Date of Patent: Jan. 15, 2013

(54) INJECTION SYRINGE PLUNGER VALVE ASSEMBLY

(75) Inventor: Kevin J Derichs, Buda, TX (US)

(73) Assignee: Animal Innovations, Inc., Houston, TX (US)

( * ) Notice: Subject to any disclaimer, the term of this patent is extended or adjusted under 35 U.S.C. 154(b) by 391 days.

(21) Appl. No.: 12/683,833

(22) Filed: Jan. 7, 2010

(65) Prior Publication Data

US 2010/0274179 A1 Oct. 28, 2010

Related U.S. Application Data

(60) Provisional application No. 61/216,247, filed on May 15, 2009, provisional application No. 61/172,827, filed on Apr. 27, 2009.

(51) Int. Cl.
A61M 1/00 (2006.01)
(52) U.S. Cl. ......................................................... 604/33
(58) Field of Classification Search .................... 604/33, 604/131, 186, 207, 218, 247–249
See application file for complete search history.

(56) References Cited

U.S. PATENT DOCUMENTS

| 4,941,809 | A | 7/1990 | Pinkerton |
| 5,015,157 | A | 5/1991 | Pinkerton |
| 5,020,980 | A | 6/1991 | Pinkerton |
| 5,044,889 | A | 9/1991 | Pinkerton |
| 5,246,354 | A | 9/1993 | Pardinas |
| 5,279,210 | A | 1/1994 | Pinkerton |
| 5,934,510 | A * | 8/1999 | Anderson ........................ 222/83 |
| 6,355,012 | B1 * | 3/2002 | Nuesch ............................ 604/74 |
| 6,989,000 | B2 * | 1/2006 | Schreijag et al. ................ 604/68 |
| 7,056,307 | B2 * | 6/2006 | Smith et al. .................... 604/207 |
| 2004/0015123 | A1 * | 1/2004 | Smith et al. ..................... 604/65 |
| 2007/0088289 | A1 * | 4/2007 | Bargh ............................ 604/207 |
| 2008/0208137 | A1 * | 8/2008 | Fago .............................. 604/191 |
| 2009/0099520 | A1 * | 4/2009 | Millman et al. ............... 604/131 |

OTHER PUBLICATIONS

US as International Searching Authority, Search Report and Written Opinion, dated Mar. 31, 2010, for PCT/US2010/20346.

* cited by examiner

Primary Examiner — Nicholas Lucchesi
Assistant Examiner — Diva K Chander
(74) Attorney, Agent, or Firm — Jones Walker Waechter Poitevent Carrere & Denegre, LLP

(57) ABSTRACT

A syringe system having a syringe with a body and a hollow barrel chamber, and a plunger shaft slidable therein, and a needle body. The syringe system includes a valve housing having a valve guide chamber with an input port fluidly connectable to a fluid pressurizing means, a storage port in fluid communication with the barrel chamber, and a discharge port in fluid communication with the needle body. A valve body is contained in the valve housing with a valve plunger slidable in the valve guide chamber. The valve plunger is slidable to a first position, where the dispensing port and storage empty port is closed and the input port and storage fill port are opened, and a second position where the input port and storage fill port is closed and the storage empty port and discharge port are opened.

14 Claims, 24 Drawing Sheets

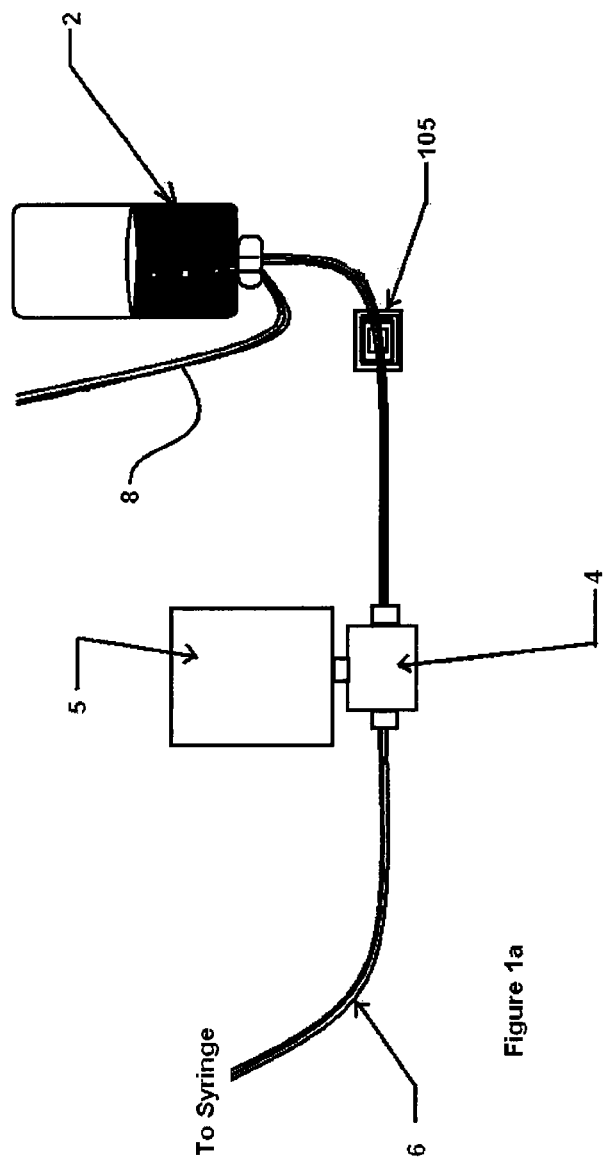
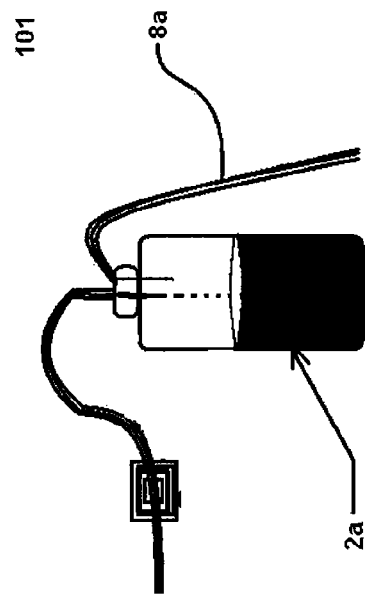
Figure 1a
Figure 1b

PLUNGER DESIGN WITH MODIFIED SE HOLE & SHORT SPRING
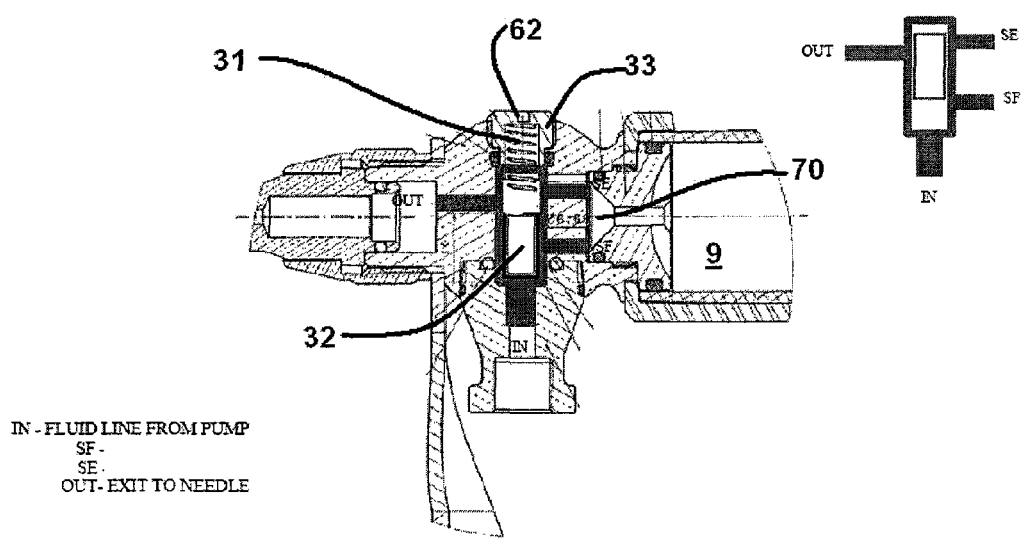
IN - FLUID LINE FROM PUMP
SF -
SE -
OUT - EXIT TO NEEDLE
Figure 13A
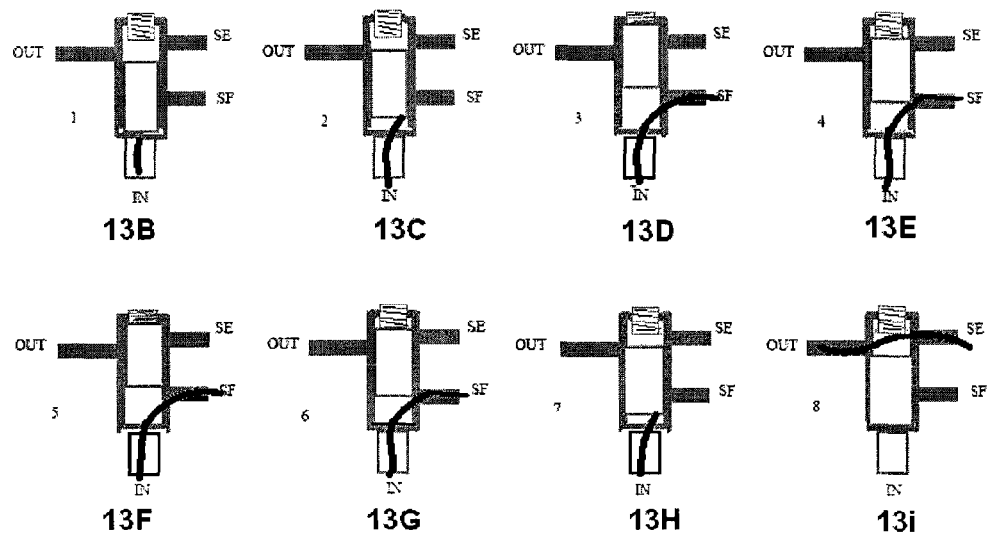
13B   13C   13D   13E
13F   13G   13H   13i

INJECTION SYRINGE PLUNGER VALVE ASSEMBLY

PRIORITY CLAIM

This application claims the priority benefit of U.S. provisional application No. 61/216,247 filed on May 15, 2009, and U.S. provisional application No. 61/172,827 filed on Apr. 27, 2009, the contents of both of which are hereby incorporated by reference.

TECHNICAL FIELD

The invention relates to valves for use in syringe injection systems.

BACKGROUND OF THE INVENTION

It is often desirable to treat large numbers of individuals or animals with a substance, such as a medication or other material, with speed, efficiency, accuracy, and accurate maintenance of records. As an example, the livestock industry requires routine vaccinating, medicating and/or treating of cattle or livestock. Failure to properly treat the animals can result in significant losses to the rancher or feedlot owner or other party responsible for the livestock. Typically, the livestock is segregated into groups according to general size and weight. It is common upon arrival at the processing station for cattle to be vaccinated for viral respiratory disease implanted with a growth stimulant, and treated for internal and external parasites. In high stress situations, antibiotics are sometimes administered simultaneously with vaccinations.

To assist in vaccination large numbers of animals, portable syringe injections systems have been developed that allow a syringe to be filled by a pump from a fill bottle, where the dose loaded into the syringe can be effectively controlled and varied as needed to tailor the injections by animal weight. Such a syringe system does not require the cumbersome filling of the syringe from a separate fluid container, allows for repeated injections, using precisely predetermined but differing dosages, and are capable of operating in a wide range of environments. One such syringe system is shown in U.S. Pat. No. 7,056,307, hereby incorporated by reference As shown in FIG. 1, a syringe system will include a fill or reservoir bottle 2, a syringe 10, a highly accurate reversible pump 4 and associated motor or drive 5, and various fluid lines between the components. The preferred system unit pump 4 is a valveless, substantially viscosity-independent pump. The pump 4 used in the preferred system is manufactured by Fluid Metering, Inc. ("FMI") of Syosset, N.Y., Models STH and STQ. To the extent necessary to understand the features and construction of the pump 4 manufactured by FMI, Applicant hereby incorporates by reference U.S. Pat. Nos. 5,279,210; 5,246,354; 5,044,889; 5,020,980; 5,015,157; and 4,941,809. A complete FMI pump cycle includes a ½ cycle of gathering fluids from the reservoir lines, and a second ½ cycle of pumping the gathered fluid out the fluid line 6 (that is, the pump is not continuously pumping fluids as would, for instance, and impeller type pump).

As used herein, the system pump 4 will be considered as a fluid pressurizing means. The pump 4 can supply positive pressures to the syringe 10 when activated to pump fluid from the reservoir bottle 2 to the syringe 10, or negative pressures (suction) when pumping fluid from the syringe 10 to the reservoir bottle 2. For purposes of this application, when the pump 4 is not active, the pump is considered as providing no applied pressure (e.g. 0 pressure) to the syringe. For purposes of this application, a dual cycle pump like the FMI pump, as long as the pump 4 is active in a forward or reverse pumping mode, is considered as supplying pressures for the entire cycle, even though for ½ cycle the pump 4 does not deliver fluid to the syringe. There are implications of this ½ cycle to the invention that will be addressed later.

To control fluid movements in the syringe, valves are used. Prior art syringes utilized check valves or spool valves. For check valves, a first check valve is located between the syringe barrel and the discharge port and is connected such that fluid flow is possible only from the syringe cylinder to the discharge port, but not a counter flow such as might occur when drawing fluid from the fluid container connected with the syringe. A second check valve allows a fluid flow from the fluid container through a supply port in the syringe to the syringe barrel when pulling back the plunger, but not when advancing the plunger. A more compact valve system is the use of a single spool valve whose relative movement alternatively blocks the supply port or discharge port, or in an intermediate position, blocks both ports. One such spool valve is shown in U.S. Pat. No. 6,989,000 (hereby incorporated by reference) and uses a flexible membrane as the movable valve member. The single check valve is more efficient, has fewer parts and allows for more readily assembly of a completed syringe.

Unfortunately, the spool valve functions as a one way valve, and hence, it is not possible to empty the syringe of fluids by reversing the fluid pump. Further, due to the many sub-components of the spool valve assembly, cleaning of the syringe usually requires complete disassembly of the complicated valve assembly, a time consuming task. To remove spool valve from the valve chamber (the void inside the metal valve housing), the valve housing must be unscrewed from the syringe head, thereby leaking medicine out of the chamber. After reassembly, fluid and air in the supply line must be purged from the line and spool valve assembly. Enabling the fluid pump will open the spool valve, opening the fluid path into the syringe barrel for purging. But squeezing the syringe handle, to purge the air from the syringe barrel out through the discharge port, sometimes causes a lockup condition. This is due to compressible air trapped on top of and in the spool valve chamber space, and the incompressible fluid below the valve, which fails to open the spool valve nose seated at the discharge port. Also, air can be trapped within the space between the flexible diaphragm and the upper plastic parts, since these are not in the immediate fluid path but are only intended to be a pressure chamber off of the main fluid path.

Additionally, the spring tension on the spool valve is set with an adjustment set screw which is inside the valve housing assembly, a poor location. If the spring tension is set for low fluid pressure at low filling speeds, the plunger fails to seat when the fluid is changed to a high fluid pressure due to high pump speed and vice versa. Hence, pressure adjustments require disassembly of part of the syringe in order to adjust spring tension, and de to lack of references for set screw position (as the spool valve may be rotating in the valve chamber with the screw) the actual degree of tension is thus set by trial an error.

Other problems associated with the spool valve include: (a) with the spool valve resting in the intermediate position (sealing both the input or supply fill port and the discharge port), extra manual pressure must be made at the syringe handle to overcome the pressure necessary to compress the spool valve spring to open the discharge port if the spool valve has been adjusted for high speed and pressure fluid filling; (b) when the spool valve is extended in the intermediate position, the spool valve will remain on the midline between the input and the discharge ports, but when fluid pressure is supplied, the terminal end of the valve may pivot off the center line and fail to realign with the open port when pressure is released, causing it to hang up on the sides of the valve chamber due to fluid viscosity, causing a lockup condition; (c) with the spool valve in the intermediate position, the syringe will not function as a manual fill syringe by means of allowing a user to pull the syringe handle back, loading fluid back in through the syringe needle into the syringe barrel. While a single valve mechanism is preferred, a valve without the limitations of the spool valve is needed.

SUMMARY OF THE INVENTION

One embodiment of the invention relates to a single valve assembly for use in a syringe in a syringe injection system. The single value is moveable in a chamber having three ports, an input port, a discharge port, and a storage fill port, located between the input discharge ports. The valve is movable between a first "fill" position with the discharge port blocked and the fill port and storage fill ports opened, and a second "discharge" position with the input port blocked, and the storage fill and discharge ports open. A third "intermediate" position may be achieved with all three ports blocked. The valve is a biased valve plunger mechanism, where the effective length or tension on the biasing member may be externally adjusted. When the pump supplies positive pressure to the syringe, the valve lifts to the first fill position, and fluid flows into the syringe storage chamber, the barrel chamber. After filling, when the pump is inactive, the valve either assumes the second discharge position, or assumes the discharge position after the application of a negative pressure from the pump. The operator then depresses the syringe plunger shaft into the barrel chamber, allowing fluids to flow from the syringe barrel chamber, to the discharge port, and out to the needle body.

A second embodiment of the invention relates to a single valve assembly for use in a syringe in a syringe injection system. The single value is moveable in a chamber having four ports, an input port, a discharge port, a storage empty port, located above the discharge port and a storage fill port, located between the input and discharge ports. The valve is movable between a first "fill" position with the discharge port and storage empty port (SE) blocked and the input port and storage fill ports opened, and a second "discharge" position with the input and storage fill ports blocked, and the storage empty and discharge ports open. A third "intermediate" position may be achieved with all four ports blocked. The valve is a biased valve plunger mechanism, where the effective length or tension on the biasing member may be externally adjusted. When the pump supplies positive pressure to the syringe, the valve lifts to the first fill position, and fluid flows into the syringe storage chamber, the barrel chamber. After filling, when the pump is inactive, the valve either assumes the second discharge position, or assumes the discharge position after the application of a negative pressure from the pump. The operator then depresses the syringe plunger shaft into the barrel chamber, allowing fluids to flow from the syringe barrel chamber out the storage empty port, to the discharge port, and out to the needle body.

BRIEF DESCRIPTION OF THE DRAWINGS

FIG. 1a depicts in block components the prior art syringe injection system.

FIG. 1b depicts in block components a bottle position for fluid recovery.

FIG. 7b, subfigures e2-e6, is a schematic showing assembly of the valve body shown in FIG. 7a.

FIG. 13a is a cross section though a second embodiment of a valve housing with four ports using a cylindrical valve plunger embodiment.

FIG. 13b-i is a cross section showing the valve body of FIG. 13a in cartoon depiction in operation from filling to dispensing.

DETAILED DESCRIPTION OF THE PREFERRED EMBODIMENTS

Figure 2:
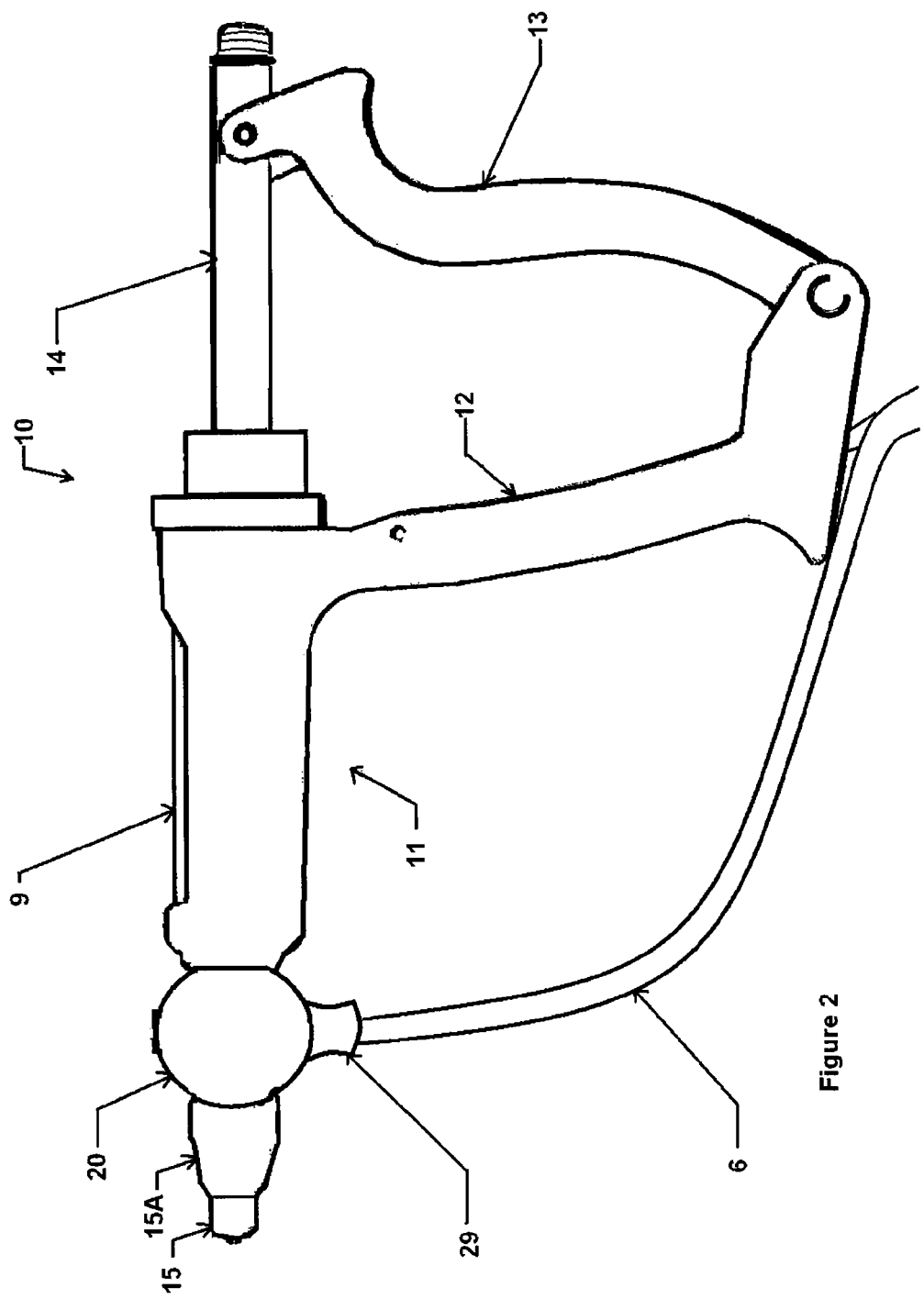
FIG. 2 is an elevation view of a syringe with valve housing.
Figure 3A:
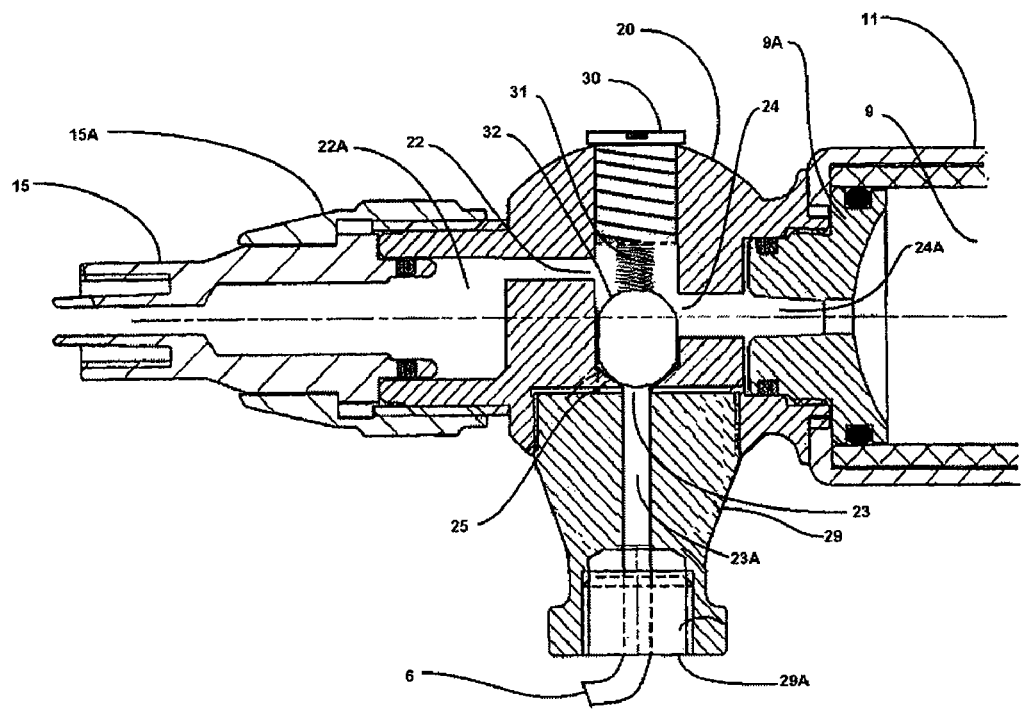
FIG. 3a is a cross section through one embodiment of a valve housing with one embodiment of a valve body shown in static position.

A schematic of one syringe embodiment is shown in FIG. 2. As shown, the syringe 10 is a includes a body portion 11 having a front grip 12 and rear grip 13, with one of the grips movable with respect to the other (here, the rear grip 13 is movable with respect to an integral front grip 12). The two gripped syringe is preferred, but not required (e.g., the plunger shaft 14 could be separately operated). The syringe body 11 includes a hollow barrel chamber 9, with a plunger shaft 14 slidable in the internal barrel chamber 9. By squeezing the two grips, the plunger shaft 14 is forced into the barrel chamber 9 to discharge fluids stored in the barrel chamber 9. At the front of the syringe body 11 is attached a valve housing 20; coupled to the valve housing 20 is a fluid line 6 and the needle body 15. An injection needle will be attached to the needle body 15 (not shown). As shown in FIG. 3A, the needle body 15 is pressed onto a front nose section of the valve housing 20 and secured with a needle lock nut 15A (see FIG. 8A), and the barrel chamber 9 has a detachable front nose piece 9A that is threaded into the rear of the valve housing 20. Sealing o-rings are used to seal the respective portions. Other means of removably attaching the needle body 15 and barrel chamber 9 to the valve housing 20 may be utilized, such a quick connects commonly used to couple fluid lines.

A cross section through one embodiment of the valve chamber is shown in FIGS. 3a-3d. The valve housing 20 is a body (stainless or aluminum is preferred) having a bore there through, the valve guide chamber 21. The valve guide chamber 21 has three ports, a discharge port 22, an input port 23, and a storage fill port (SF) 24. As shown, the storage port fill channel 24A is intermediary the discharge port 22 and the input port 23. Each port is associated with a channel: channel 23A communicates with a fluid supply line 6 (when attached), channel 22A communicates with the needle body 15, and channel 24A communicates with the barrel chamber 9. As shown, the input port 23 includes a lower seat 25 (see FIG. 8B). Positioned in the upper end of the valve guide chamber 21 is the valve body 30, later described. As shown, the valve housing 20 includes an attached flow line connection member 29, with the channel 23A there through, terminating with a flow line connector 29A to accommodate the fluid line 6. Flow line connector 29A can be a quick connecter or other type of fluid line connection. The fluid connector member 29 may also be unitary with the valve housing 20.

Figure 4:
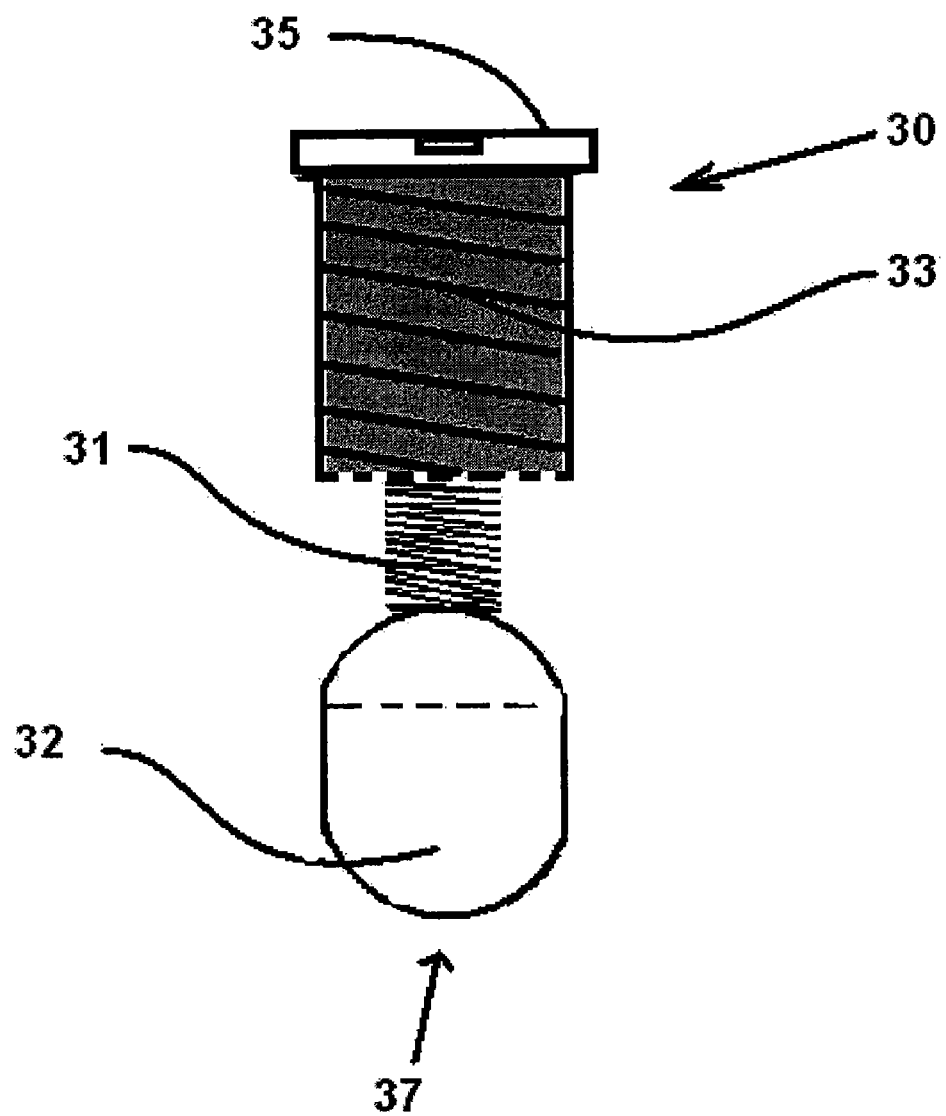
FIG. 4 is an elevation view of one embodiment of a valve body with a spherical shaped top and bottom valve body, with a cylindrically shaped center body.

Located at the upper end of the valve guide chamber 21 is the valve body 30, which, as shown, is threaded into the top end of the valve guide chamber 21. A detail of this embodiment of the valve body 30 is shown in FIG. 4. As shown, the valve body 30 consists of a valve plunger 32, an insert body 33 and a biasing member 31, coupled to the insert body 33 at one end, and the valve plunger 32 at the other end. As shown, biasing member 31 is a spring, but could also be a resilient expandable/contractible solid or other biasing body. The biasing member 31 may be removably fixedly attached or rotatably attached to valve plunger 32 and insert body 33, or simply coupled.

Figure 6A:
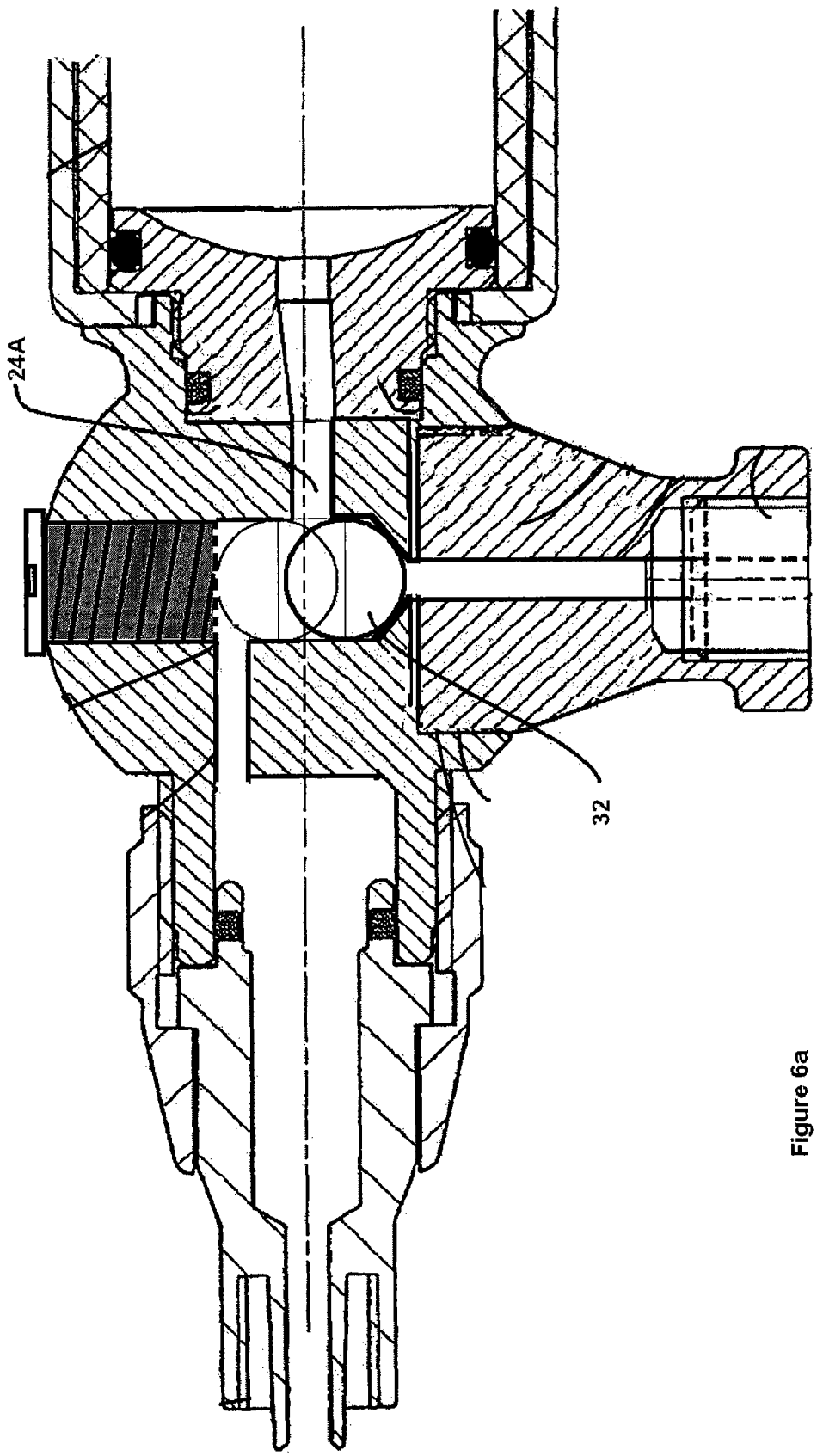
FIG. 6a is a cross section through a third embodiment of a valve housing with one a spherical embodiment of a valve plunger valve shown in static position.
Figure 6B:
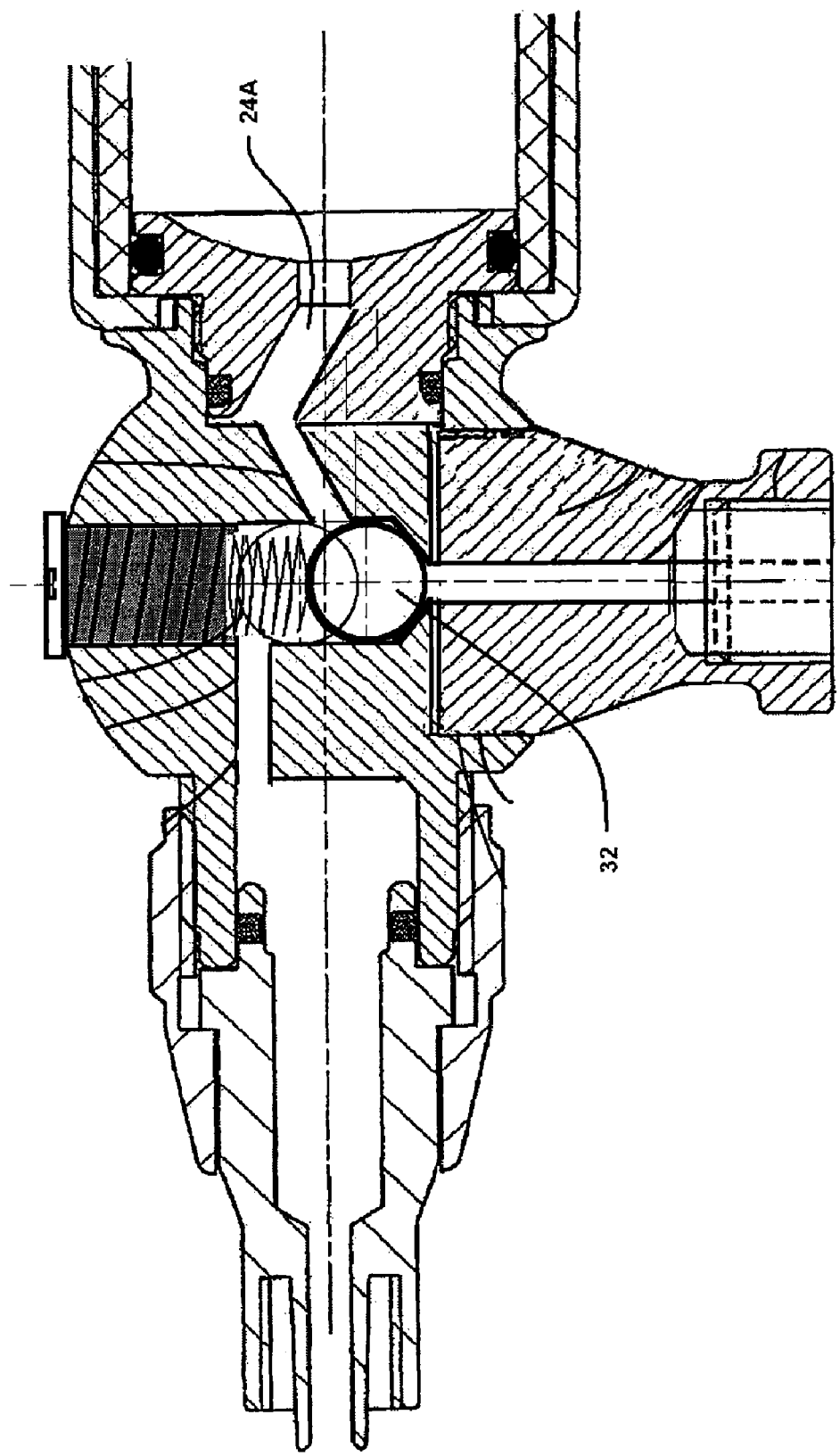
FIG. 6b is a cross section through a fourth embodiment of a valve housing having angled channels with one a spherical embodiment of a valve plunger valve shown in static position Cross section through one embodiment of a valve housing with one embodiment of a valve body shown in dispensing position.

As shown, valve plunger 32 is cylindrically shaped and the lower end of the valve plunger 32 forming a hemispherically shaped seating surface 37, but other valve plunger shapes and lower seat 25 geometries could be used, such as a spherically shaped valve plunger (see FIGS. 6A and 6B, FIG. 6B also depicts an angled channel 24A), a cylinder with a tapered seating end or a flat seating end, provided the lower seat 25 of the input port 23 is shaped to seal or close against the valve plunger seating surface 37. If the valve guide chamber 21 is a shaped chamber (for instance, oval in cross-section), the valve plunger 32 will be comparably shaped and slidable (but not necessarily rotatable) in the valve guide chamber 21. The valve plunger components can be made from different possible material such as molded plastic, PTFE (Teflon), stainless steel or other chemically inert materials. Other materials will be apparent to those of skill in the art. The side wall of the valve guide chamber 21 or the valve plunger 32 or both may be made or coated with materials that reduce friction, such as a PTFE coating, or a self assembled monolayer (SAM) material coating.

The threaded attachment of the insert body 33 (see FIG. 4) into the valve guide chamber allows the position of the valve body 30 within the valve guide chamber 21 to be easily modified with a set screw head 35. This arrangement is one means to adjust the position of the valve body 30 in the guide chamber 21. As shown, this adjustment means (here the threads) is positioned on the insert body 33. An O-ring 34 may be used to seal against the valve guide chamber 21.

Operation of the Valve.

A. Static Position—No Applied Pressure Regime

The static position of the valve body 30 in the guide chamber 21 is that position assumed when the syringe 10 is empty, or the pump is not active. The actual static position will depend on the length of biasing member 31 (hereafter described as a spring). A long spring may be used so that the valve body's 30 static position is with the valve plunger 32 seated on the seat 25 of the input port 23, as shown in FIG. 3a. With the long spring, the location of the ports and length of the valve plunger are such that the static position closes the input port 23 and the storage fill port 24, with the remaining ports in fluid communication through the valve guide chamber 21. As used herein, a port is considered "open" if there is a second port in fluid communication with the "open" port; contra-wise, a port is considered "closed," such as blocked by the valve plunger, if the "closed" port is not in fluid communication with any other port.

Figure 3B:
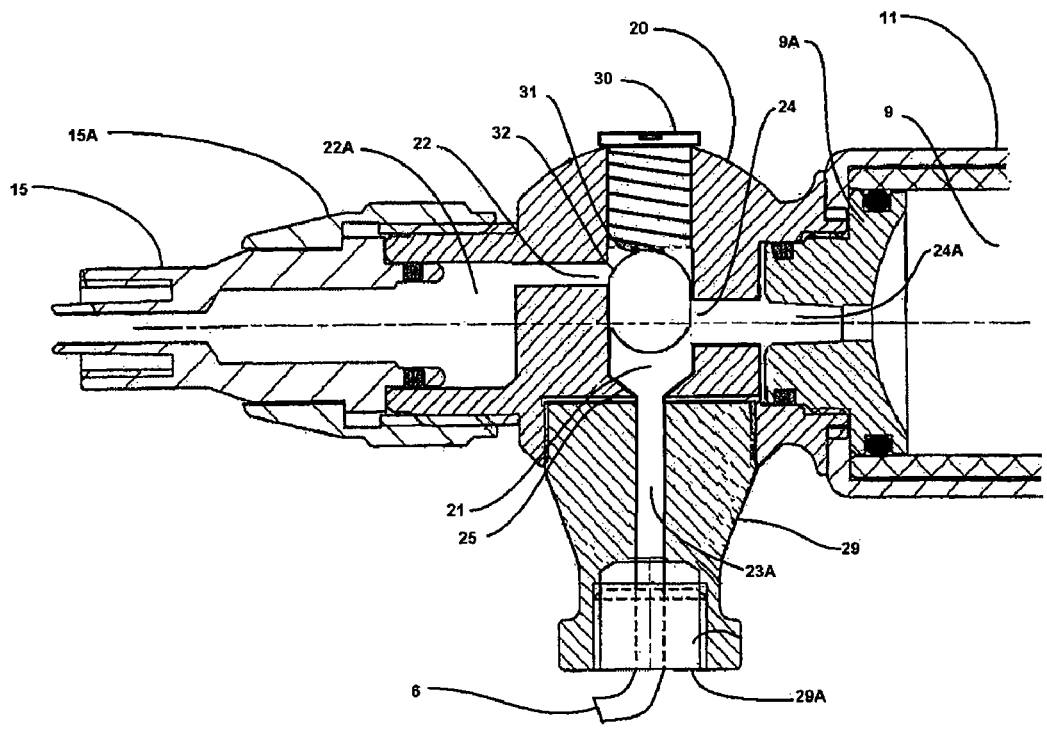
FIG. 3b is a cross section through one embodiment of a valve housing with one embodiment of a valve body shown in fill position.
Figure 3C:
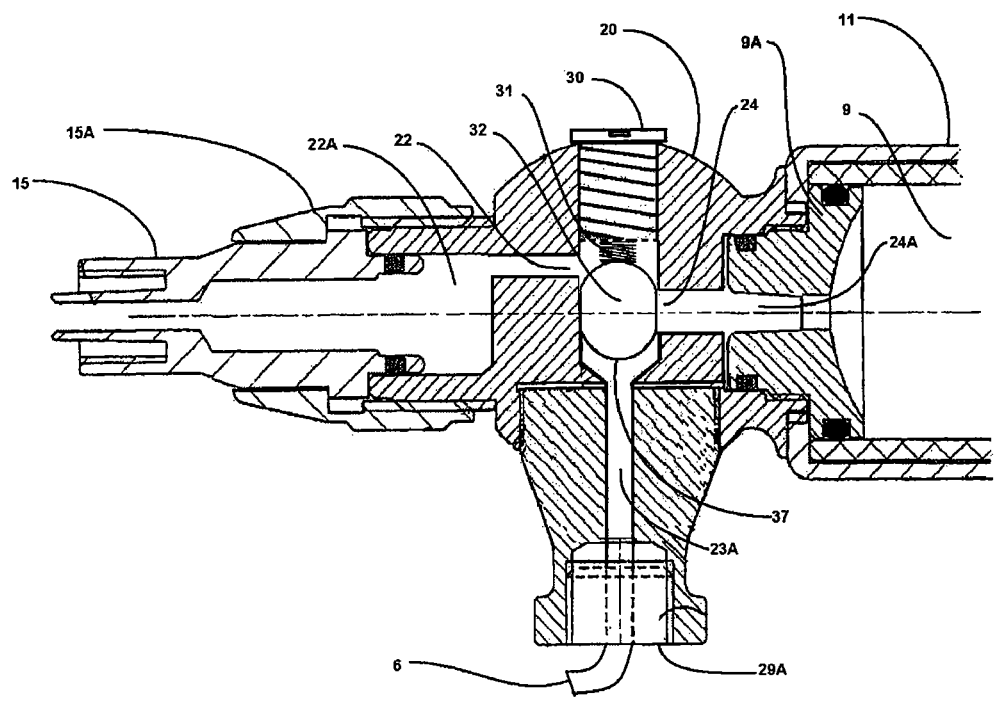
FIG. 3c is a cross section through one embodiment of a valve housing with one embodiment of a valve body shown in intermediate position.

A second embodiment uses a shorter spring 31, so that in the static position, the valve plunger 32 is the intermediate position, as shown in FIG. 3c. In the intermediate position, the input, storage, output and discharge ports are effectively closed (e.g. not in fluid communication with another port) by the valve plunger 32. There may be minor leakage around the valve plunger body 32 when fluid is present in the syringe. To minimize fluid leakage, the tolerances between the walls of the guide channel 21 and the valve plunger body 32 should be close.

B. Fill Position

In operation, the syringe 10 begins with the valve body 30 in the static position (either position shown in 3a or 3c, depending on the selected spring length), with no fluids stored in the syringe. To fill the syringe 10, the fluid pump motor 5 is activated, and fluid is extracted from the reservoir bottle 2 and flows through the fluid line 6 to the flow line connection 29A. Fluid enters the valve body 30 and flows up channel 23A to exit the input port 23. Sufficient surface area of the valve plunger lower seat surface 37 is exposed to the incoming fluid so that the spring bias is countered by the pressure exerted by the pumped fluid, thereby compressing the spring 31, and lifting the valve plunger 32 from the static position. The valve plunger 32 will move in the valve guide chamber 32 until the storage fill port 24 is opened, placing the valve in the fill position, shown in FIG. 3B. The length of the plunger valve 32 is sufficiently long to effectively block or close the discharge port 22 while filling, as shown in FIG. 3b.

At this point, the pumped fluid is transferred to the syringe barrel chamber 9 in the syringe body 11. The spring 31 must be weak enough to compress in response to the exerted fluid pressure. Spring tension can be effectively modified by threading the insert body 33 further into the valve guide chamber 21 to increase the spring compression, or backing out the insert 33 to decrease spring compression.

When the fluid pump motor stops, the externally applied positive fluid pressure ceases, and the applied pressure on the valve plunger 32 will drop, hence, the spring 31 will decompress. Note that this has implications on the location of the storage fill port 24. When a dual cycle pump 4 is active, but in the ½ cycle where pumping to the input port 23 ceases, the spring 31 will begin to decompress. Hence, the storage fill port 24 must be located sufficiently below the uppermost location of the valve plunger 32 to remain closed as the spring 31 expands during this ½ cycle.

When the pump 4 is de-activated and not supplying a positive pressure, the valve plunger 32 will move downwardly in the valve guide chamber 21. The valve plunger 32 will initially achieve the intermediate position (all ports blocked) shown in FIG. 3c. With the short spring, the valve plunger 32 stops in this intermediate position. With the longer spring, if there is little leakage of fluid around the valve plunger 32, the valve plunge 32 will effectively stop in the intermediate position, as further downward motion of the valve plunger 32 is resisted by the incompressible fluid volume located below valve plunger 32 (with all ports blocked, fluid located below the valve plunger cannot migrate). If there is sufficient leakage around the unseated valve plunger 32, the spring may slowly continue to decompress until the valve plunger 32 seats, achieving position 3d, the discharge position. The intermediate stopping point is preferred, but is not necessary.

C. Dispense Position

Figure 3D:
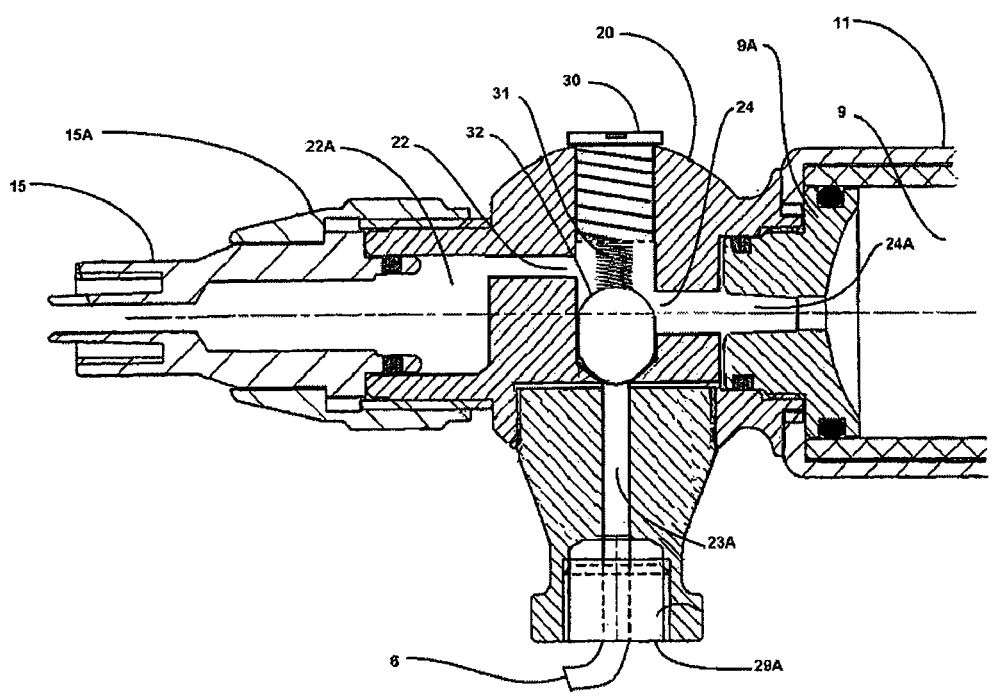
FIG. 3d is a cross section through one embodiment of a valve housing with one embodiment of a valve body shown in dispensing position.

To dispense fluid, the valve body must be in the discharge position shown in FIG. 3d. here the input port 23 is blocked, while the discharge port 22 and storage fill port 24 are opened. To ensure that the discharge position is achieved, the pump 4 is run in reverse for a short period of time. By briefly reversing the motor 5 (e.g., a single reverse pulse of the pump) a "negative" pressure or a suction will be formed in the fluid fill lines, drawing the valve plunger 32 to the seat 25, closing the input port 23 and opening the discharge port 22. When the motor is deactivated after this reversal, the plunger valve 32 will remain seated, as the fluid lines to the pump are closed, thereby maintaining the negative pressure at the input valve 23.

Dispensing fluids then comprises manually squeezing the syringe grips or handles 12 and 13, which moves the plunger shaft 14 into the barrel chamber 9. This movement forces fluid from the barrel chamber 9, through the channel 24A into the guide chamber 21, and out the discharge port 22 to channel 22A and thence through the needle body 15 to the attached needle. This movement also will help keep the plunger valve 32 seated against the seat of the input port 23.

D. Fluid Recovery

Figure 5:
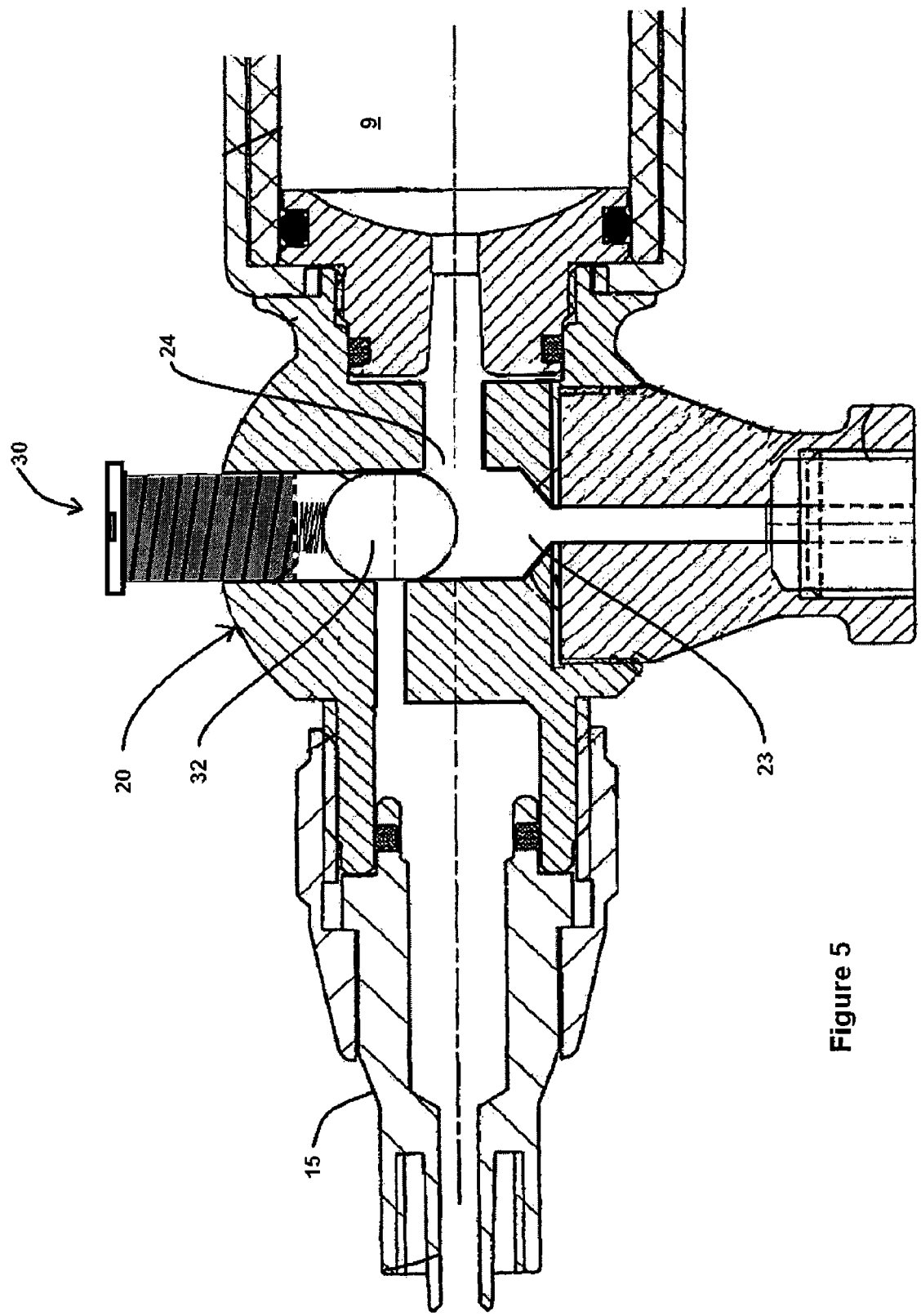
FIG. 5 is a cross section through a second embodiment of a valve housing with one embodiment of a valve body shown in fluid recovery position.

After dispensing is complete, any remaining fluid in the syringe and fluid lines can be extracted by sufficiently backing out the insert body 33, as depicted in FIG. 5, and running the motor 5 in reverse. In this position, the valve plunger 32 blocks the discharge port 22, but the storage fill port 24 and input port 23 remain opened. With the insert sufficiently partially removed from the guide chamber 21, even with downward movement of the valve plunger 32, the storage fill port 24 will remain open. It is not generally necessary to completely remove the insert body 33 plunger body 30 for fluid extraction, as it is only necessary that the valve plunger 32, when subject to a suction from the pump, does not expand sufficiently to block the storage fill port 24. The valve plunger 32 must be maintained sufficiently above the storage fill port 24 to keep the storage fill port 24 open, while closing the discharge port 22 is blocked (i.e. maintain the valve plunger is the "fill" position). Partial removal of the insert body 33 is sufficient, and the amount of "removal" can be determined during calibration of the syringe.

Once the valve plunger 32 is properly positioned, the motor, in reverse mode, extracts the fluid from the barrel chamber 9, through the valve guide chamber 21, back through the fluid lines to the up-righted storage bottle in position 2a, where the displaced air in the bottle is pushed out through the air vent 8a. In the event of leakage around the valve plunger 32, the contaminated needle should be removed before this procedure is undertaken to prevent possible contamination of fluids returned to the reservoir bottle.

The syringe 10 may have a check valve or manually operated vent into the barrel chamber 9 to assist in fluid extraction. As later described, a check valve may also be contained in the shaft plunger 14.

E. Manual Operation

The syringe may also be operated manually if a long spring is utilized (or with a short spring by threading the insert body 33 into the valve guide chamber 21 until the valve plunger 32 seats on the input port 23). In this configuration (see FIG. 3A), the syringe 10 is loaded or filled by placing the needle in a fluid container holding fluid to be dispensed, with the grips 12 and 13 in a discharge position (plunger shaft 14 inserted into the barrel chamber 9). To load, the grips 12 and 13 are separated, creating a suction through the syringe 10 and drawing in fluids through the needle. The manually loaded device is discharged in the usual fashion—squeezing the grips 12 and 13, drawing the plunger shaft 14 into the barrel chamber 9 to discharge fluids through the syringe. Hence, the device can still operate independently of a pump.

Other Embodiments

Figure 7A:
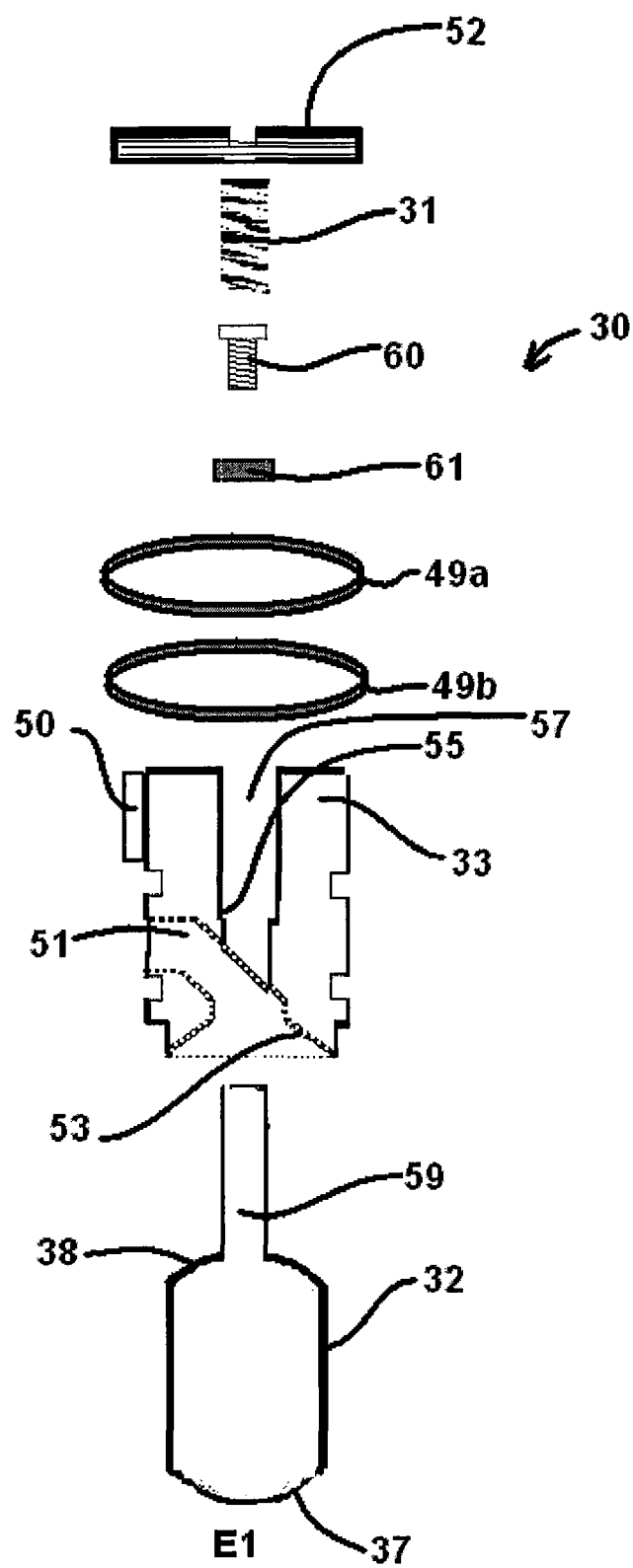
FIG. 7a is an exploded view, partially in cross section, of one embodiment of a valve body.
Figure 7B:
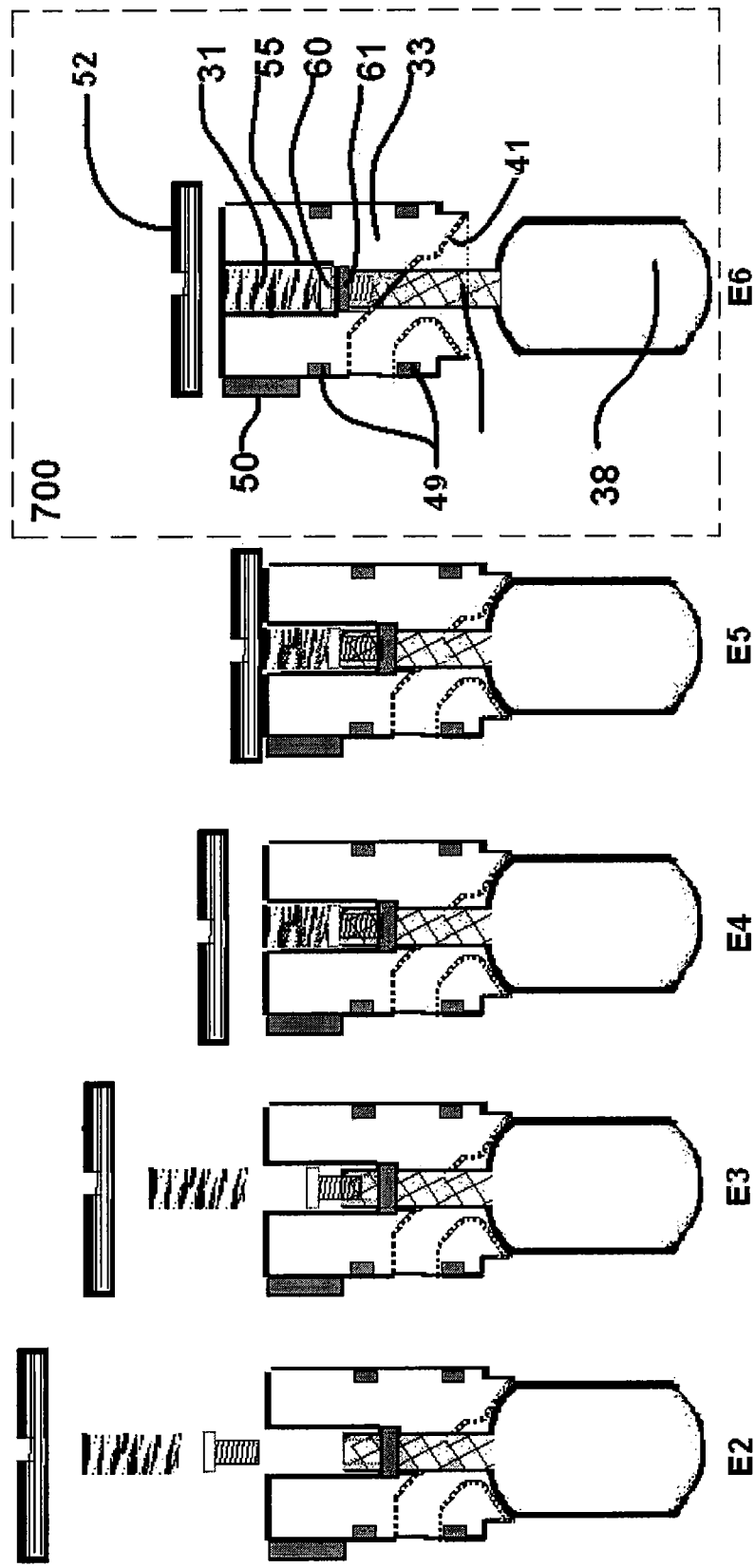

Another embodiment of the valve body 30 are shown in FIGS. 7a and 7b. As shown, valve body 30 consists of an inset body 33 that that pressed into the valve guide chamber 21, and has a key 50 to orient the insert body 33 into the guide chamber 21. O-rings 49a and 49b may be used to seal the insert body 33 in the guide channel 21. To accommodate valve body 30, upper end of valve guide chamber 21 includes a notch 64 and a lip 62 formed in the chamber sidewall (see FIG. 8A). When the insert body 33 is inserted into the guide chamber 21, the key 50 slides in the notch 64, and the insert body 32 rests on the lip 62. A protective cover 52 (which may include a gasket, not shown) is be attached to the upper end of the guide chamber 21 to retain the valve body 30 within the valve guide chamber 21. For instance, the protective cover 52 may be threadably attached to the valve guide chamber 21.

Insert body's 33 lower end forms an upper seat 53. Insert body has a center bore 57 that runs from the upper seat 53 through the body, and the center bore narrows at ridge 55. A side channel 51 runs from the center bore 57 through the sidewall of the insert body 33. When the insert body 33 is keyed into position in the guide chamber 21, side channel 51 aligns with the discharge port 22 of the guide chamber 21.

Plunger valve 32 is again shown as a cylindrical body, having upper 38 and lower 37 seating surfaces shaped to accommodate the upper seat 53 of the insert body, and lower seat 25 of the input port 23 respectively. Valve plunger 32 includes an upstanding nose 59 that is internally threaded to accommodate set bolt or set screw 60. Stop ring 61 is an annular ring that is slidable in the upper center bore 57, but cannot pass ridge 57. Upstanding nose 59 of valve body 32 is slidable in interior opening of stop ring 61. Stop ring center opening, however, will not pass screw head of set screw 60. Hence, plunger valve 32 is retained in insert body 33 by the set crew 60 and stop ring 61. The inability of the set screw head to pass through stop ring 61 limits the downward movement of plunger valve 32.

Figure 11:
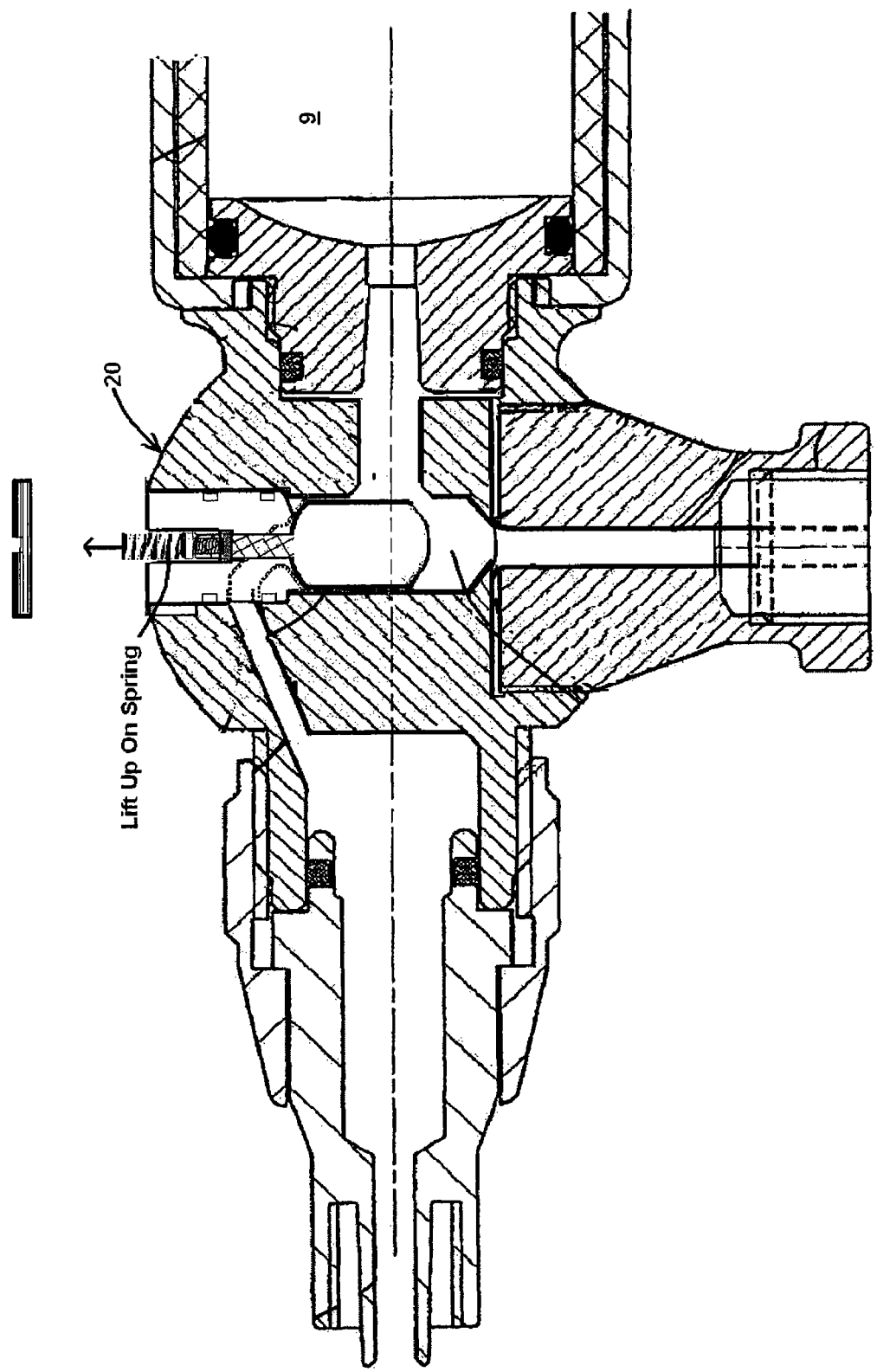
FIG. 11 is a cross section through one embodiment of a valve body with a valve plunger.

Positioned in the center bore 57 is a biasing member 31 (depicted as a spring). In the embodiment shown in FIG. 7a, spring is positioned between the protective cover 52 and set screw 60. Hence, spring 31 biases set screw 60, and hence valve plunger 32, downwardly. Spring may be attached to the valve plunger 32, on one end and the set screw/cover on the other end. Alternatively, spring may free float between the valve plunger 32 and set screw/cover (that is, is attached to neither), or may be attached at only one end, i.e., attached to the valve plunger or the set screw/cover. Preferably, the spring is connected to at least the set screw or cover, to ease fluid recovery operations. An O-ring may be included below stop ring to seal against upstanding nose 59 of valve plunger 32. With the set screw 60 threaded into the upstanding nose 59, a fine adjust of valve plunger 32 extension into the valve guide chamber 21 can be made. By adjusting this extension, the tension on the spring in compression can also be adjusted to account for different fluid pressure regimes. Hence, this configuration is another means to adjust the position of the plunger valve 32 in the guide chamber 21. Additionally, the spring or biasing member 31 may be attached to the set screw (for instance, distal end of spring may be retained below top of set screw, not shown), and in this instance, the spring 31 and the screw 60 can be manually lifted (see FIG. 11) to maintain the valve plunger 32 in a position against the upper seat (the fill position) to facilitate the process of fluid extraction from the syringe by pump reversal, as previously described.

Figure 8A:
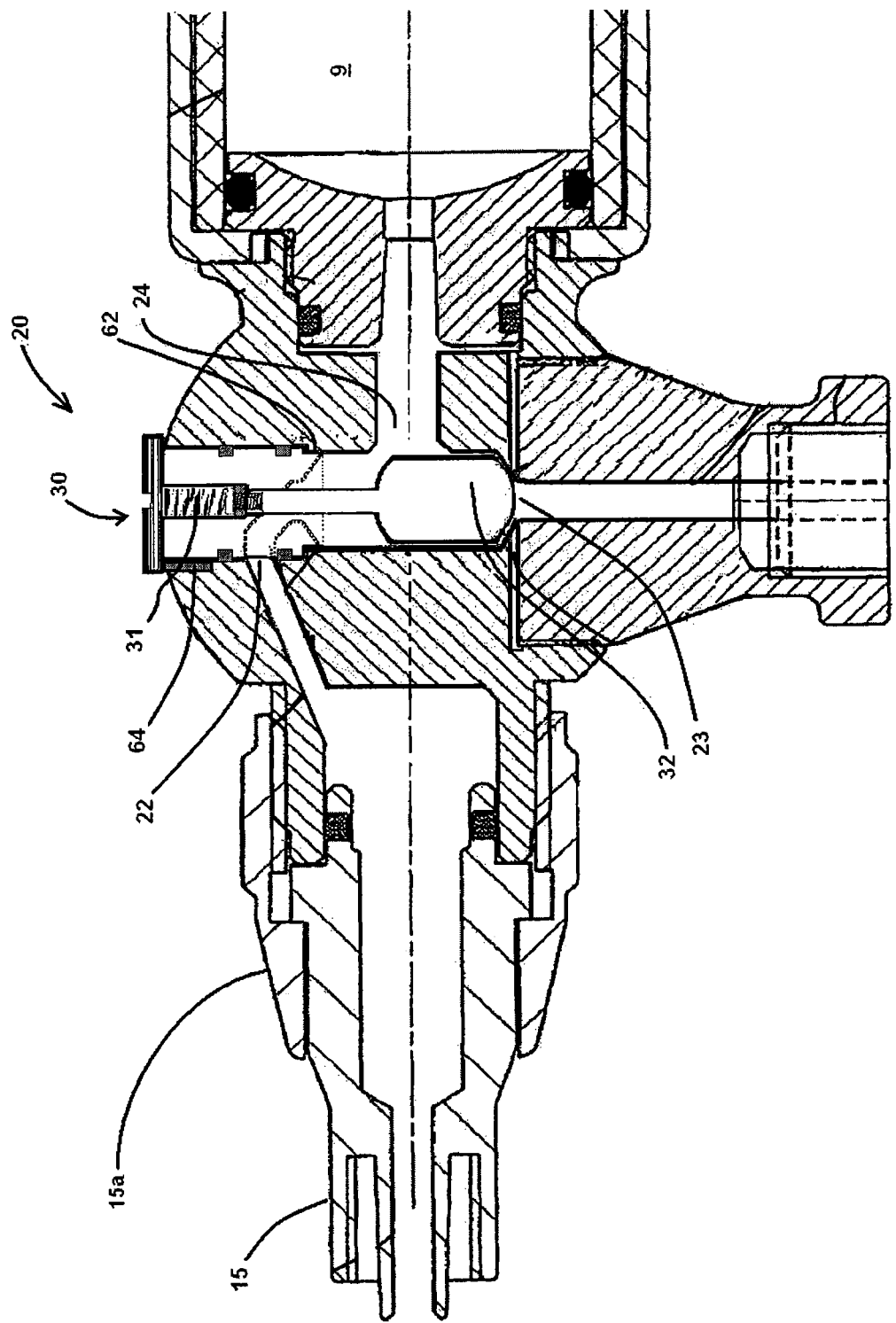
FIG. 8a is a cross section through one embodiment of a valve housing with the valve body embodiment of FIG. 7a shown in static or dispensing position.
Figure 8B:
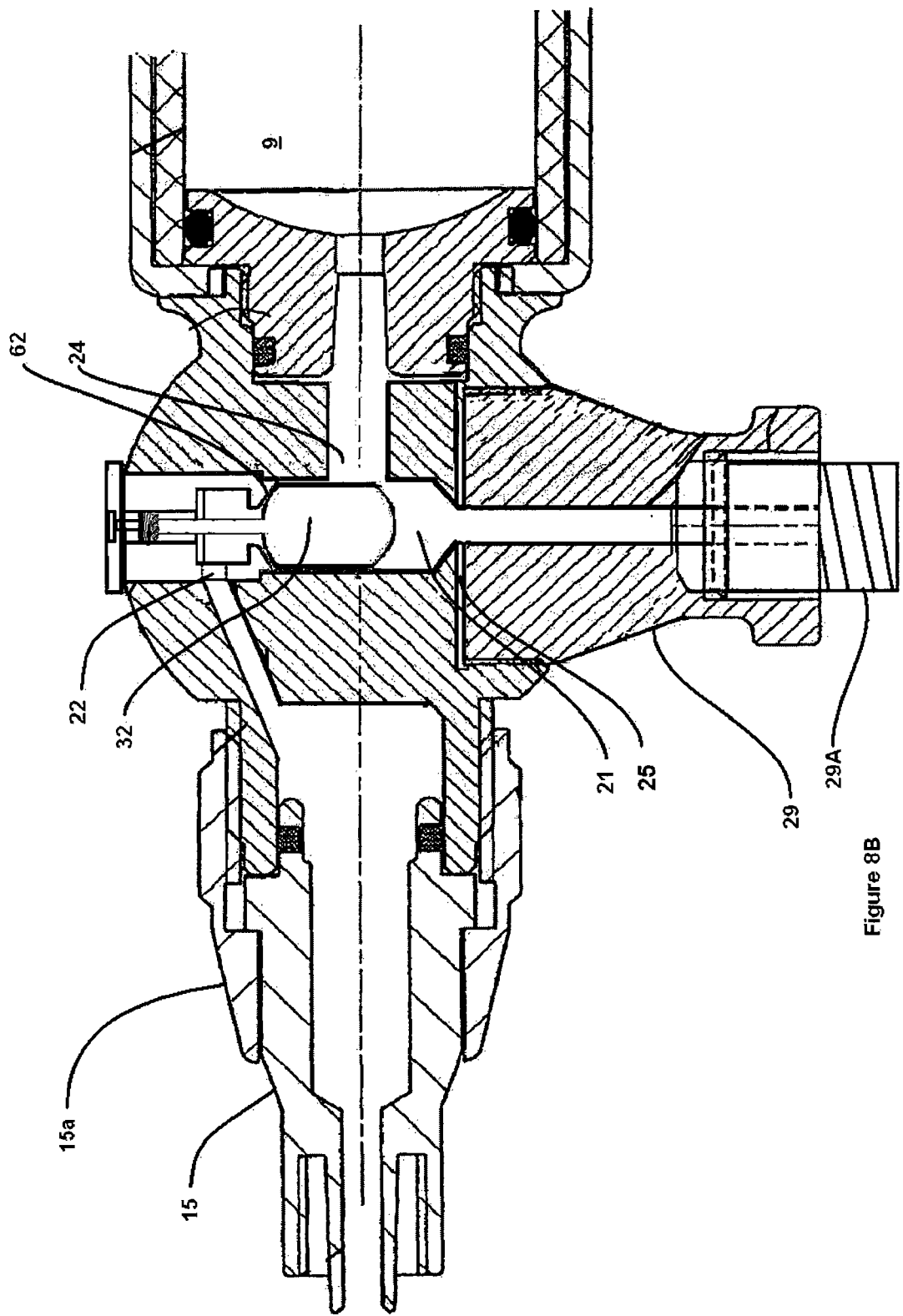
FIG. 8b is a cross section through one embodiment of a valve housing with the valve body embodiment of FIG. 7a shown in fill position.
Figure 9A:
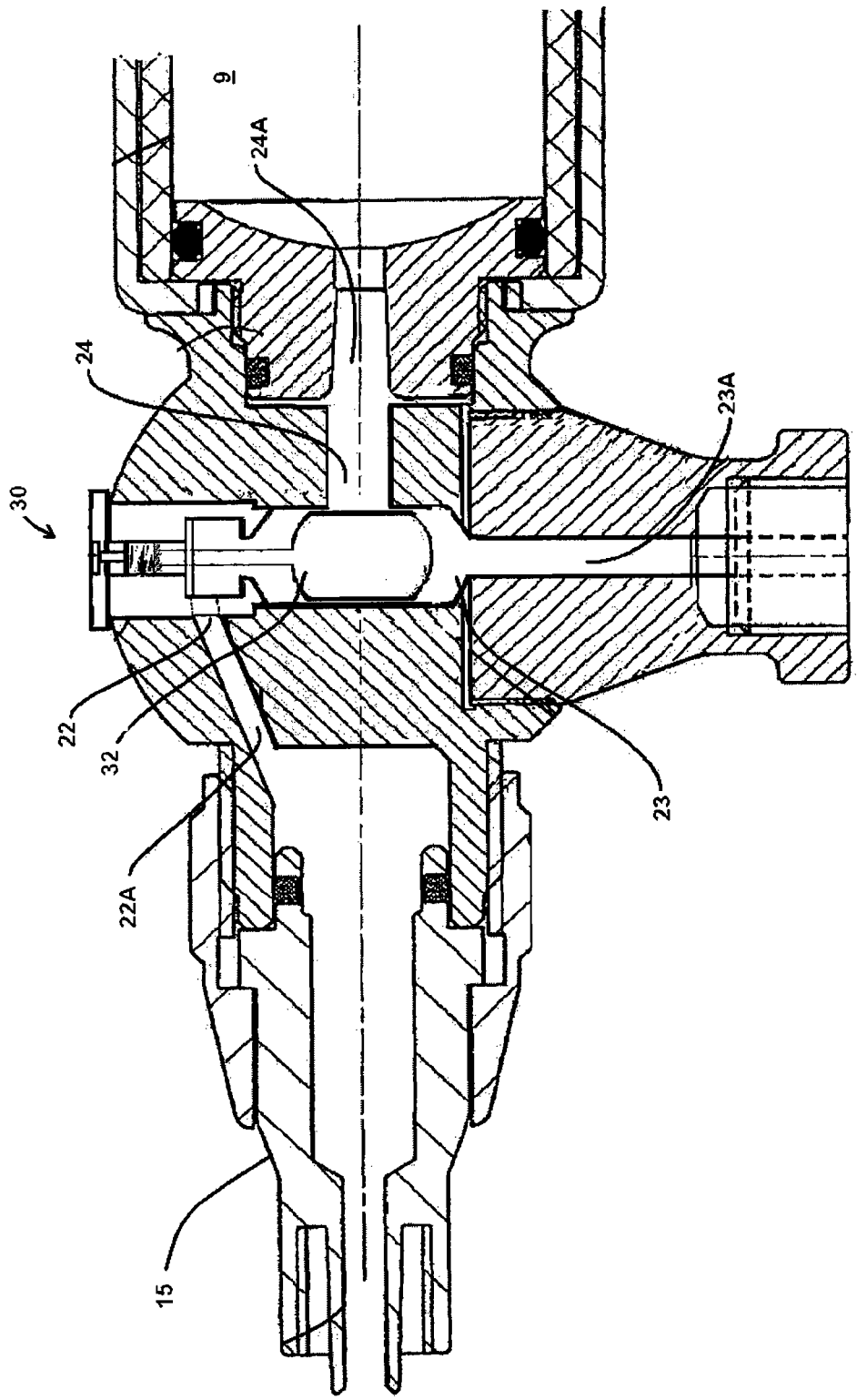
FIG. 9a is a cross section through one embodiment of a valve housing with the valve body embodiment of FIG. 7a shown in intermediate position.
Figure 9B:
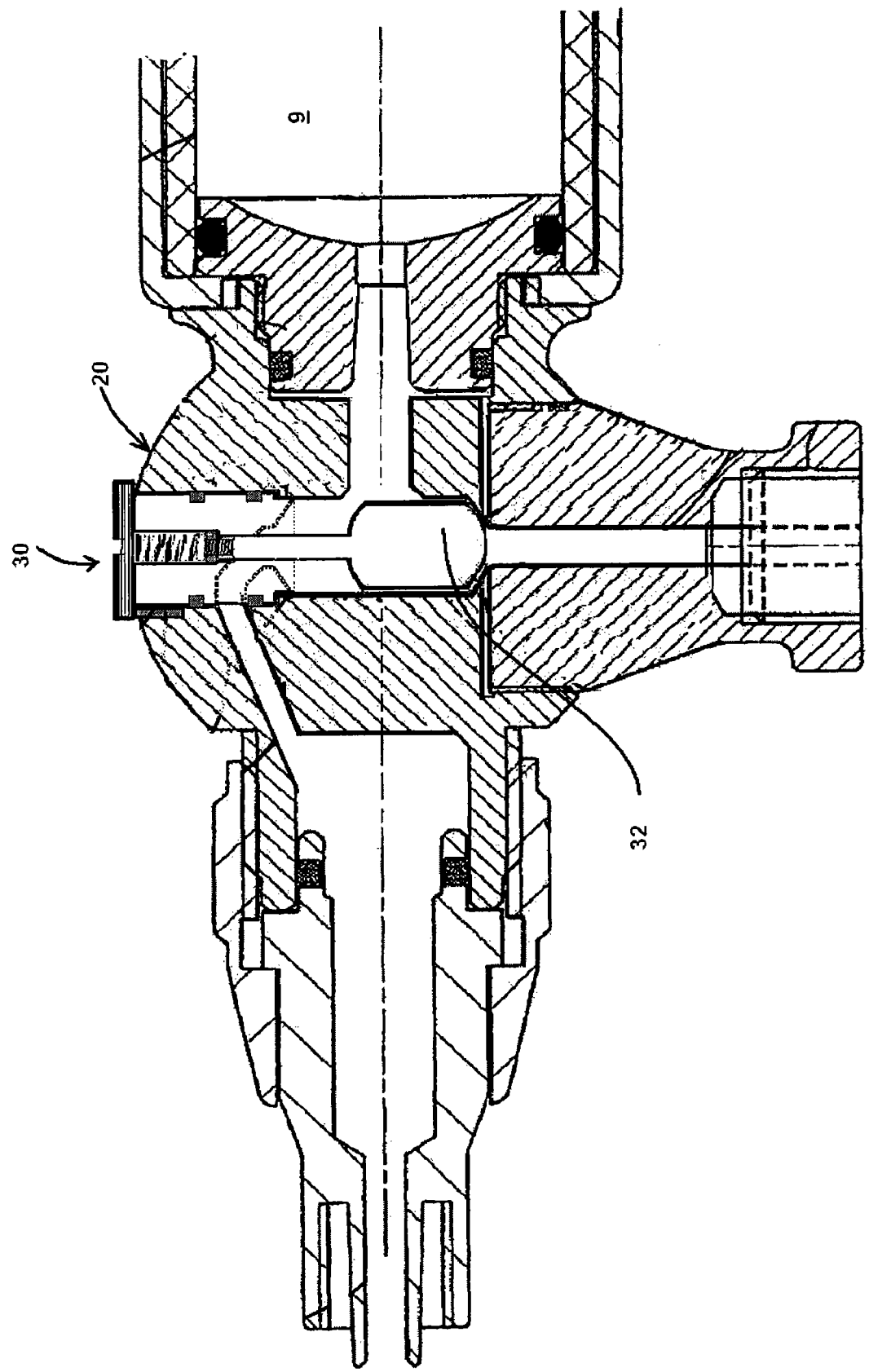
FIG. 9b is a cross section through one embodiment of a valve housing with the valve body embodiment of FIG. 7a shown in dispensing position.
Figure 10:
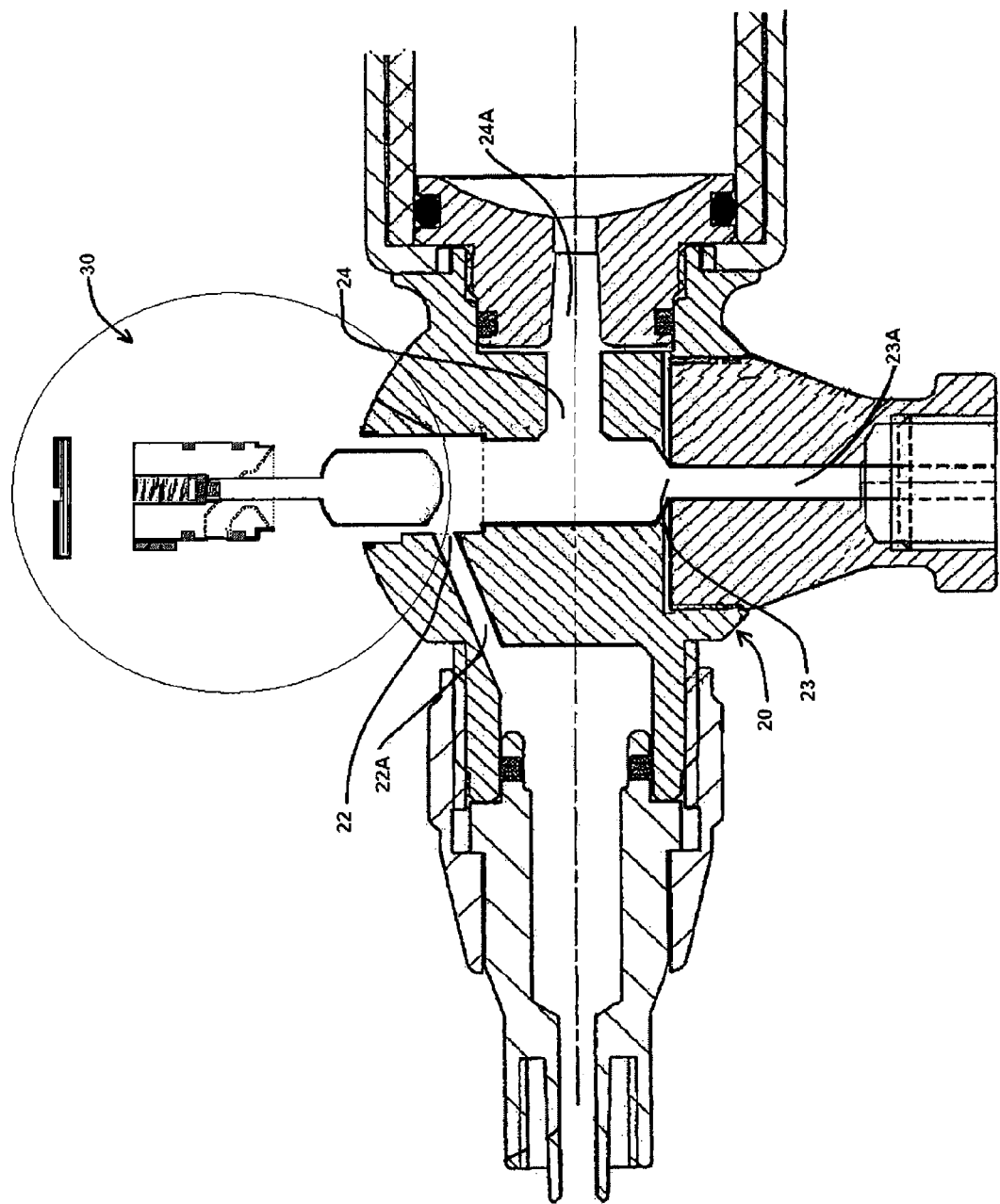
FIG. 10 is a cross section through one embodiment of a valve housing with the valve body embodiment of FIG. 7a shown in partial disassembly for cleaning.

In this embodiment, the static position of the valve body is shown in FIG. 8a, with the valve plunger 32 seated against lower seat 25. As in the first embodiment, incoming fluid exerts pressure against the seated plunger 32 to oppose the spring biasing force and lift the seated plunger 32, until storage fill port 24 is uncovered and opened (see FIG. 8b). Once the external positive pressure is removed (pump is deactivated) the biasing force of biasing member 31 will extend the valve plunger 32 downwardly in the guide chamber 21 to either the intermediate position (FIG. 9a, achieved if leakage or seepage past the valve plunger 32 body is minimal) or to a seated position against the input port seat 25 (see FIG. 9b). In either event, to dispense fluid, it is preferred to run the pump in reverse mode for a short period of time to ensure the valve plunger 32 is in the discharge position, that is, seated against lower seat 25.

Figure 12:
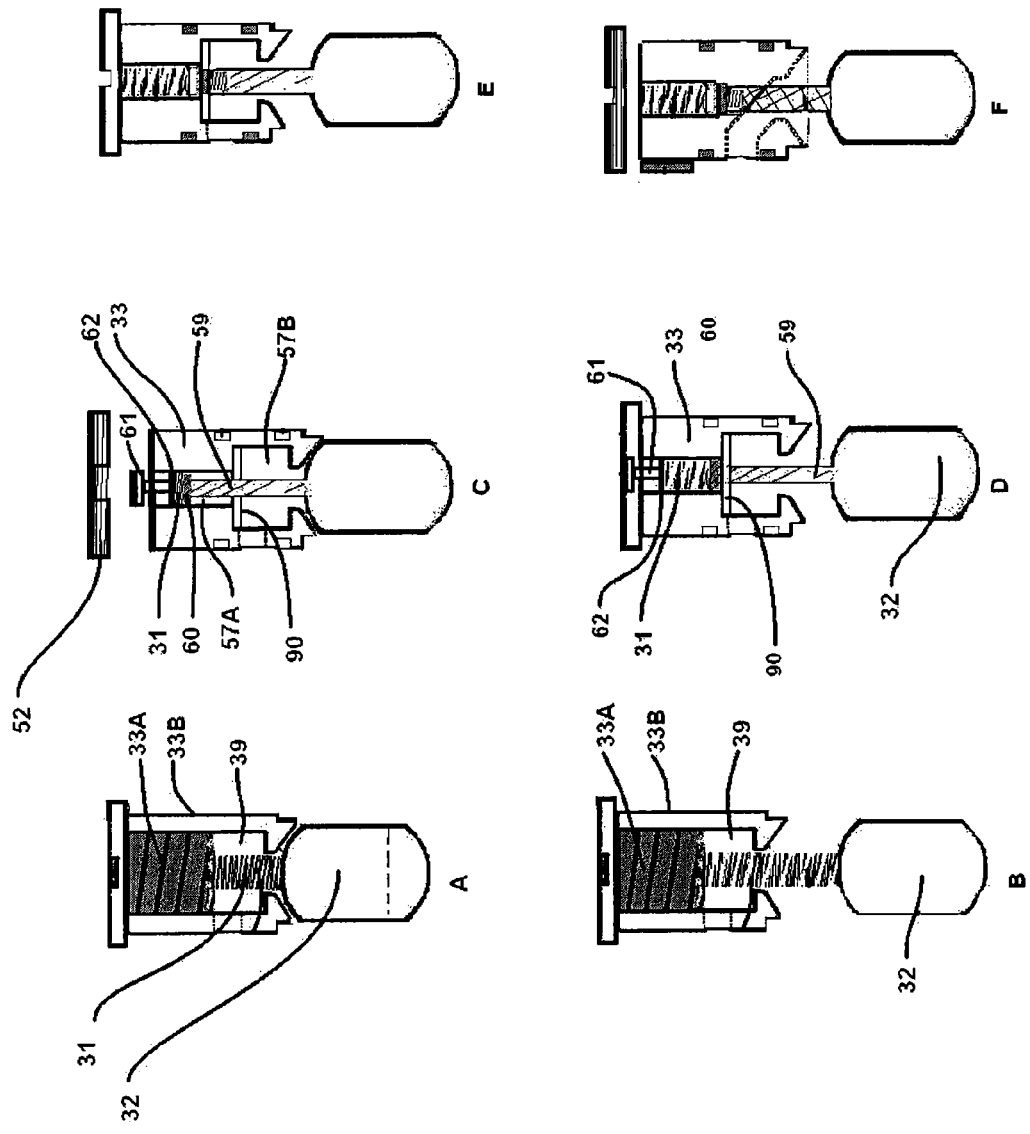
FIGS. 12a & 12c are a cross section through other embodiments of the valve body in the first position.
FIGS. 12b & 12d are a cross section through other embodiments of the valve body in the static or second position.
FIGS. 12e & 12f are a cross section through other embodiments of the valve body in the static or second position.

Alternatively the spring 31 may be suspended from the keyed insert body 33, for instance, by threading the an interior insert body 33A into the exterior insert body 33B, such as shown in FIGS. 12A and 12B. In this instance, valve plunger 32 may include upstanding nose 67 (not shown), with spring 31 disposed around the nose, preventing possible spring distortion. As shown, the insert body 33A has center bore 39 that is large to accommodate interior insert body 33A.

Shown in FIGS. 12C and 12D is another variation of the valve body. In this variation, the insert body 33 center bore has a top bore area 57A and bottom bore area 57B. The two areas are separated by a plate body 90 that is pressed in, and has a center opening to accommodate the plunger nose 59. As before, a screw or bolt 60 is threaded into the neck or nose 59 of the plunger body 32. This embodiment includes a second screw or bolt 61. Bolt 61 threads though a washer body 62, slidable in upper chamber 57A. The biasing member 31 is trapped between washer body 62 and bolt 60. By adjusting screw 61, the tension on the spring 31 may be adjusted. The protective cover 52 retains the valve body assembly in the valve guide chamber. As before, this configuration including the screw 60, represents another means to adjust the position of the plunger valve in the guide chamber.

FIGS. 12E and 12F show another variation in the valve body 30. The valve body 30 in FIG. 12F is that depicted in FIG. 7, while the valve body in 12E differs from that of FIG. 12F only in the insert body, the insert body 33 is that depicted in FIGS. 12C and 12D.

Four Ported Guide Chamber

Figure 15A:
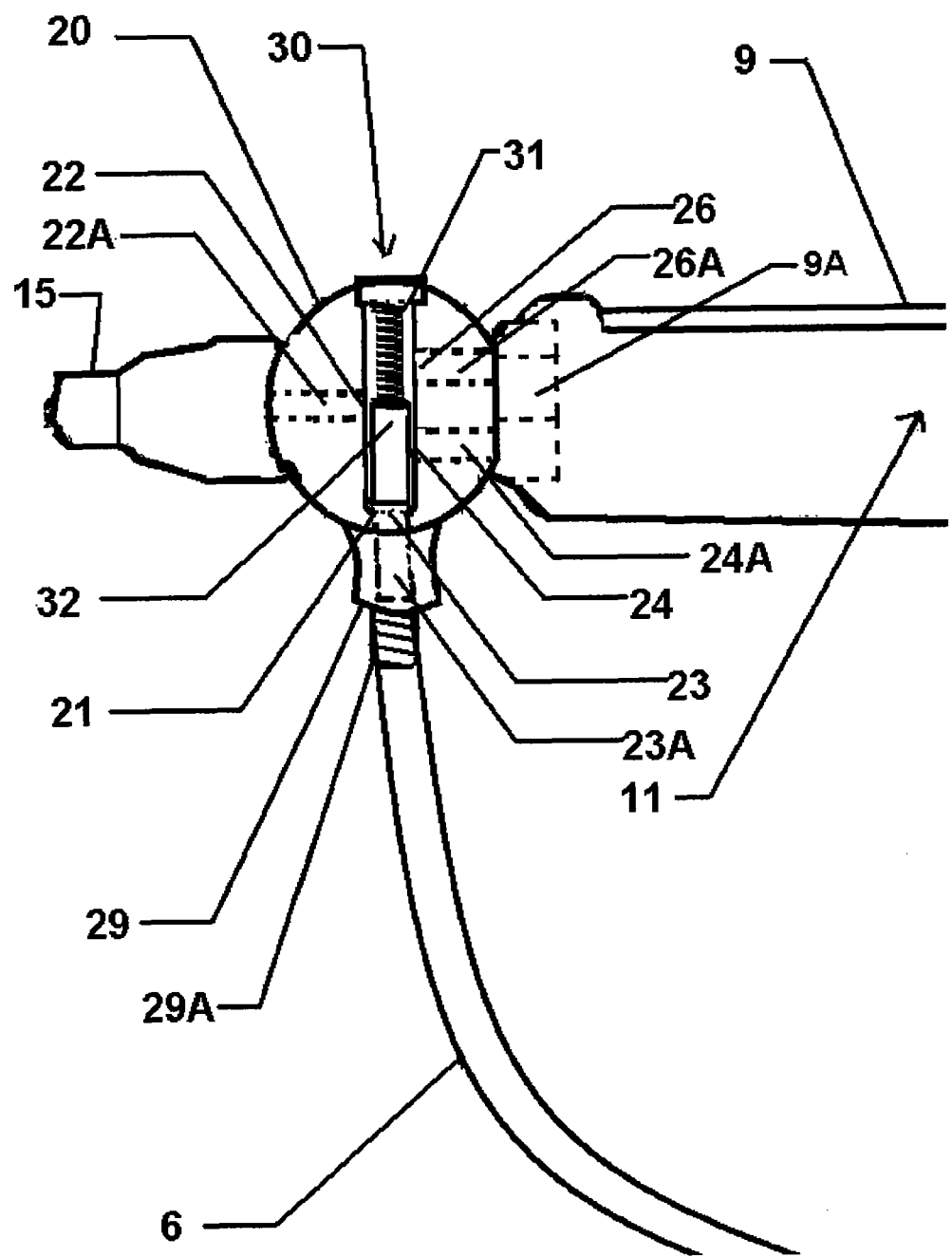
FIG. 15a is a cross section through a four port embodiment of the valve body in a static, resting position using a long biasing members.

Variations in on the guide chamber 21 may be used. For instance shown in FIG. 15A is a guide chamber 21 having four ports and four associated channels: an input port 23, a discharge port 22, a storage fill port (SF) 24 and a storage empty port (SE) 26. As shown, the order of the ports vertically is the SE port 26 (uppermost), the discharge port 22, the SF port 24, and the input port 23 (lowermost). The SE and discharge port can be at the same level or the SE port may be slightly above the discharge port and the SF may be at the same level as the input port 23. What is preferred is that the SE port be located sufficiently lower in the guide chamber 21 than the uppermost blocking extension of the valve plunger 32 in the fill position, so that the SE port remains closed during a dual pump's ½ cycle of fluid gathering, as is better explained by FIG. 13, later described. This is not a concern with a continuously pumping device.

Figure 16:
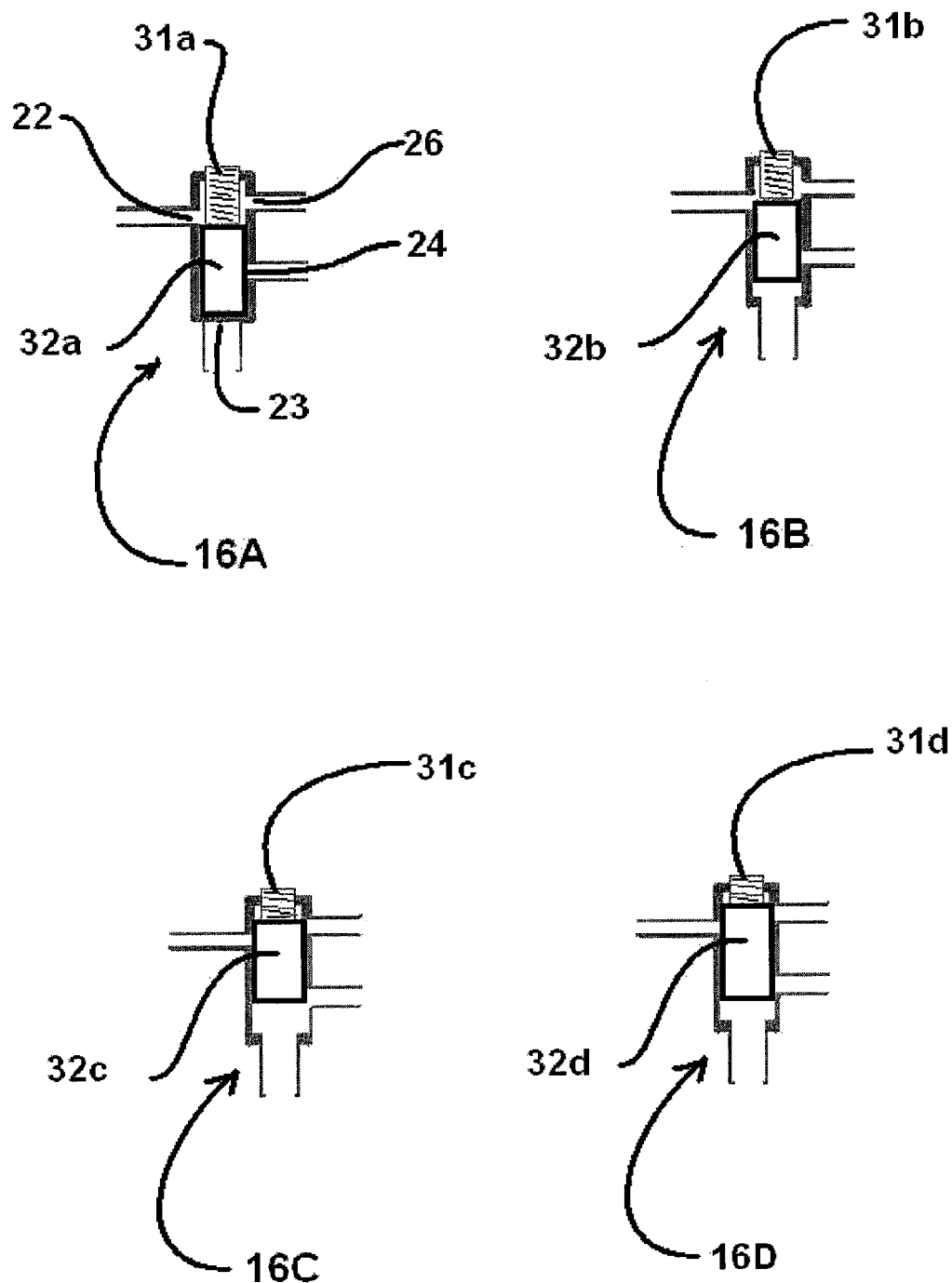
FIG. 16a is a cartoon depiction of a four port valve embodiment in the static position with a long spring.
FIG. 16b is a cartoon depiction of a four port valve embodiment in the static position with an intermediate length spring.
FIG. 16c is a cartoon depiction of a four port valve embodiment in the static position with a short spring length.
FIG. 16d is a cartoon representation of a short spring embodiment using a longer length plunger, in the static position, to close all four ports in a four port embodiment

As shown, the channels associated with the SE and SF ports merge into a single channel 70 before entering the barrel chamber 9 (see FIG. 13A); however, each port (SE, SF) may have a completely isolated channel into the barrel chamber 9. In the embodiment shown, the valve plunger 32 is a cylinder, with the seat 25 being a flat. Biasing member 31 is positioned above the valve plunger 32 and supported by insert body 33, much as the embodiment of the valve body shown in FIG. 4. A screw threaded through a biasing disk 62 may be located at the top of the center bore to allow for adjustment of the spring tension, or to position of the valve plunger 32 in the guide chamber 21. Operation of the valve body during filling and discharge is depicted in FIGS. 13D-13I and will be described using a short biasing member. Preferably, the length of valve plunger 32 is sufficiently short to allow closure of only one of the SE and SF ports at a time (i.e. not to close the SE and SF ports simultaneously) to achieve an intermediate position shown in FIG. 16C. A longer length plunger may be used (see FIG. 16d), where all ports are blocked. FIGS. 16A, 16B and 16C depict possible static conditions for this valve embodiment, depending on the chosen spring length (16A depicts a long spring, 16B an intermediate length spring, and FIG. 16C, a short length spring). Note that the intermediate length spring may not be long enough to have all ports blocked, or alternatively, the plunger may not be long enough to block all ports, that is a portion of the SE port may remain open in the intermediary position. To accommodate different fluid pressures, spring bias or spring rate may need to be adjusted (either by setting spring tension though an adjustment, or by using a spring with the desired properties). The short spring configuration shown in FIG. 13E is preferred, and in this position, the valve plunger 32 does not totally block the SF port under static conditions (pump not activated).

Figure 15B:
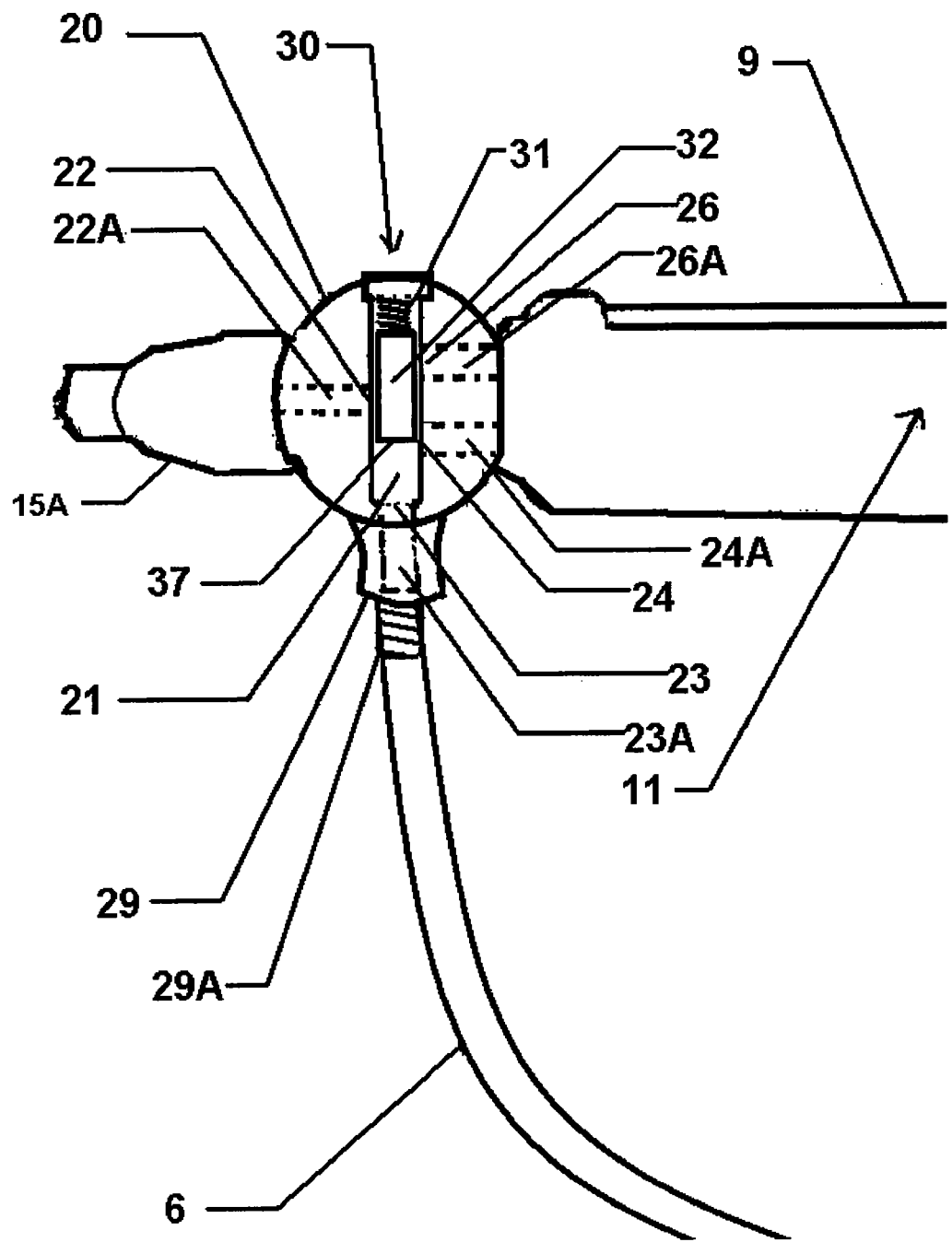
FIG. 15b is a cross section through a four port embodiment of the valve body in fill position, or in static position using a short spring.
Figure 15C:
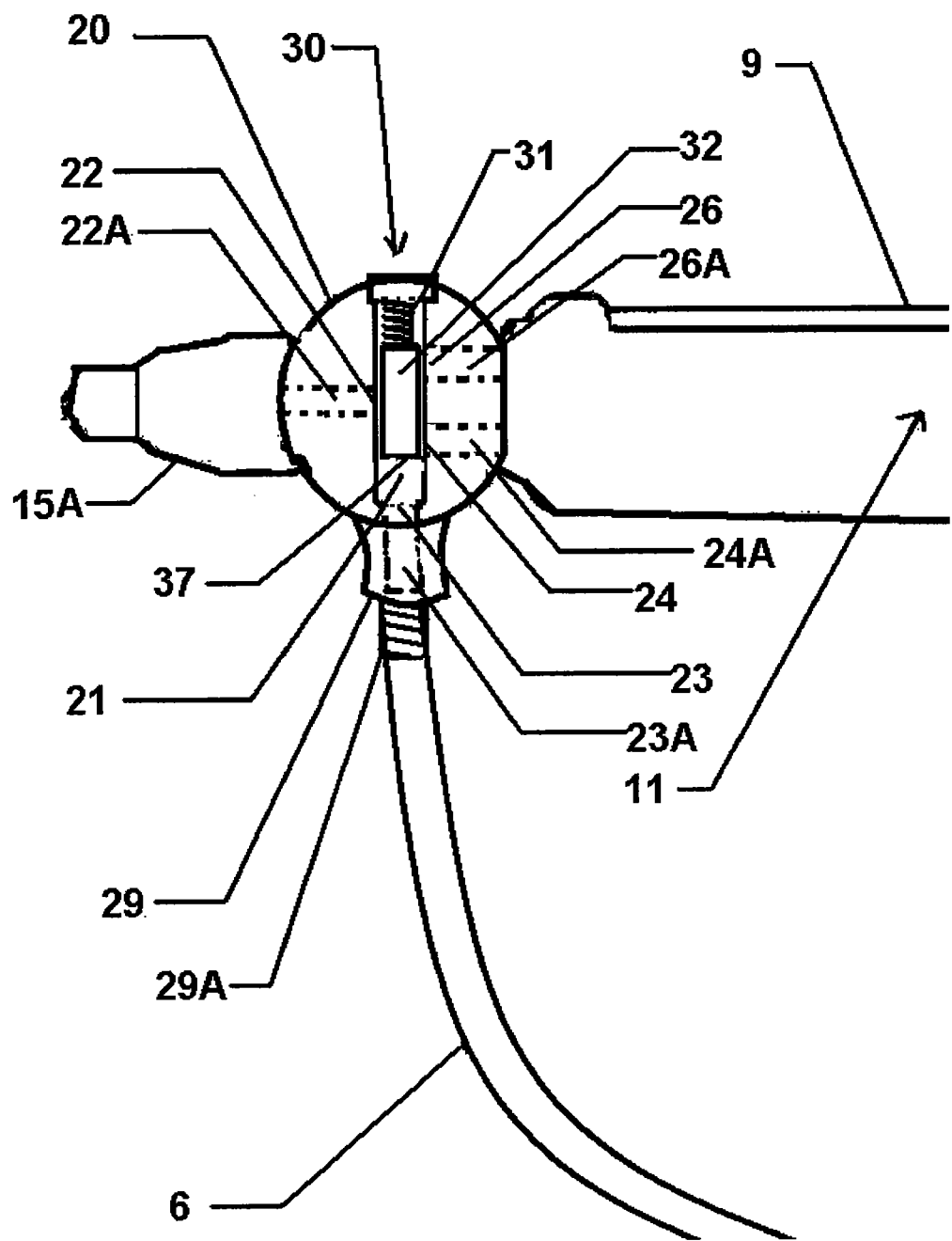
FIG. 15c is a cross section through a four port embodiment of the valve body in an intermediary position/static position using an intermediary length spring.
Figure 15D:
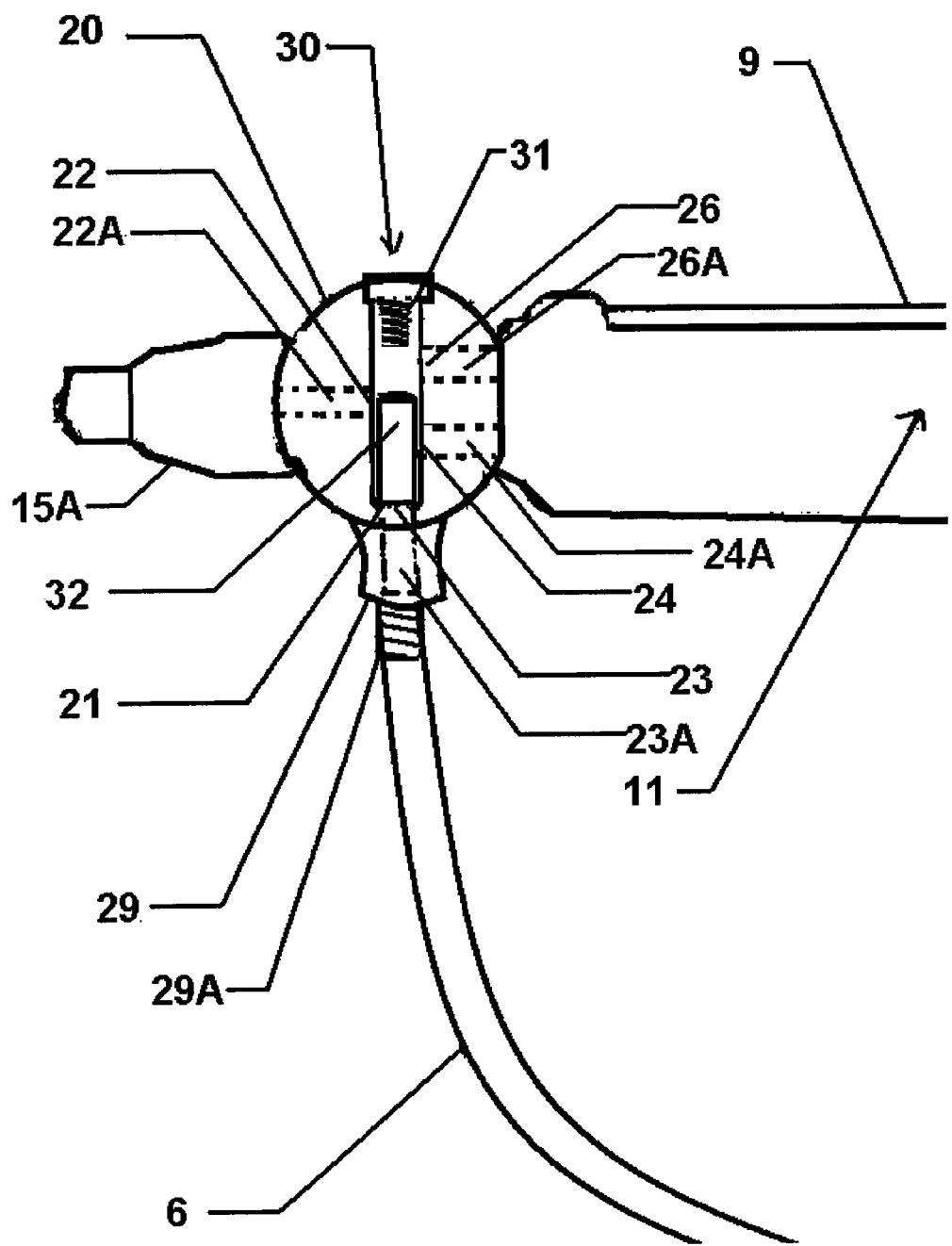
FIG. 15d is a cross section through a four port embodiment of the valve body in a dispense or discharge position.

Beginning at any of the static positions, to fill the syringe 10, the pump 4 is started in the forward direction, and fluid is pumped into the valve guide chamber 21 through the input port 23. The pumped fluid will exert a positive pressure and compress the biasing member 31 until the SE port is opened (partially or fully), allowing fluid to enter the barrel chamber 9. This position is represented by FIGS. 15B, and 13D. At completion of the fill operation, the pump is stopped, resulting in no applied pressure, and the biasing member will decompress. The valve plunger 32 will return to: (a) the intermediate position (shown in FIG. 13H, and also in FIG. 15C) if a long spring or intermediate spring is used (assuming only minor leakage around the plunger); or (b) to position 13B if a long spring is used (13B or 15A with leakage around the plunger); or (c) to position 13E or 15B is a short spring is used. To dispense fluid, the pump is preferably run in reverse at least one cycle to exert a negative pressure on the input port 23, to ensure the valve plunger 32 is seated (FIGS. 15D and 13I), thereby closing both the SF and input port 23. The reverse pump cycle may not be needed if the long spring is utilized and leakage occurs around the valve plunger 32. At this juncture, the input port and SF port are blocked, while the SE and discharge port are opened. Squeezing the syringe handles thus will dispense fluid from the barrel chamber, through the SE port to the guide chamber, and out the dispense port to the attached needle (FIG. 13I and FIG. 15D (note FIGS. 13I and 13B are the same position).

The valve position throughout a full pumping cycle employing a ½ cycle pump is depicted in FIG. 13B-13I in a short spring four ported embodiment. The valve positions through the pumping cycle are as follows: FIG. 13B spring not touching plunger, plunger in static (or manual position); FIG. 13C spring not touching plunger, motor staring to turn pushing plunger up; FIG. 13D spring compressed touching plunger, fluid filling syringe during first ½ turn; FIG. 13E spring un-compressed pushing plunger down (to intermediate position), 2nd ½ turn pulling out of bottle; FIG. 13F spring compressed touching plunger, fluid filling syringe during 3rd ½ turn; FIG. 13G spring un-compressed pushing plunger down (to intermediate position), 24th ½ turn pulling out of bottle; FIG. 13H spring not touching plunger, motor starts turning backwards creating negative pressure in the fluid line and under the piston; and FIG. 13I spring not touching plunger, plunger seated, fluid dispense and manual operation.

Fluid Recovery

Figure 14:
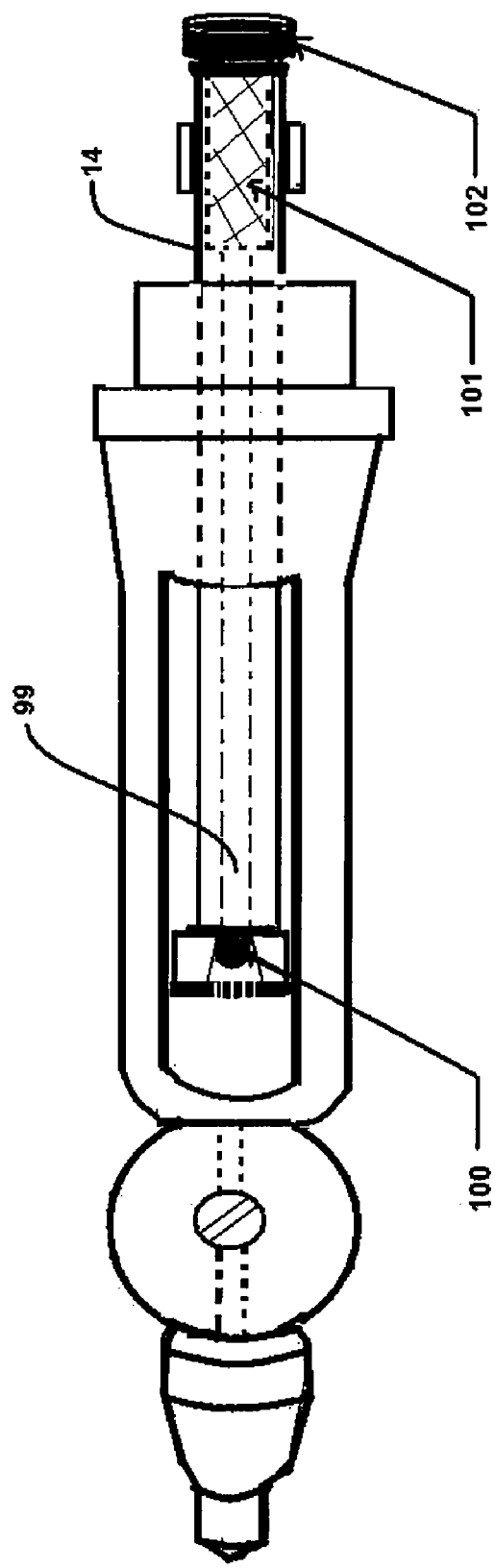
FIG. 14 is a cross section though a plunger shaft detailing a hollow plunger and check valve.

In the four ported embodiment, where the static position leaves the SF port partially opened (FIG. 13E), fluid recovery is easily achieved. Fluid recovery is assisted with the use of a check valve 100. The check valve can be mounted on the syringe body into the barrel chamber (preferably near the end of the chamber closest to the valve body), but it is preferred to mount the check valve on the plunger shaft 14, particularly for the four port embodiment. Such a configuration is shown in the top partially cutaway view of FIG. 14. As shown, the plunger shaft 14 is hollow or has a channel 99 there through. Located at the interior end of the plunger shaft 14 is a check valve 100. As shown, check valve is located on the interior end of the plunger (the end within the barrel chamber). Check valve 100 is designed to open when a suction is applied in the interior of the barrel chamber 9, and check valve 100 should be more responsive to a negative pressure than valve plunger 32 (that is, check valve 100 will open in response to pressures that would not move plunger shaft 32). Check valve 100 could also be located within the plunger shaft 14 or the exterior end of the plunger shaft 14, but this is not preferred, as fluids can now enter the hollow plunger shaft, an undesired result. Also shown is an air filter cartridge 101 inserted in the plunger to prevent contamination from incoming air, and a sealing cap 102 that is threaded onto the end of the plunger shaft to seal the channel 99.

After a dispense operation, it is easy to recover fluid in the system when a short spring is employed. In this instance, the valve body 30 is in a static configuration with the SF port partially or totally opened (see FIG. 13E). Hence, to recover fluids, the operator would remove the sealing end cap 102, invert the reservoir bottle (see FIG. 1b) and operate the motor/pump in reverse. In response to the negative pressures, check valve 100 opens, and fluid is withdrawn from the barrel chamber 9, through the open SF port 24, to the input port 23, and then back to the reservoir bottle 2a. Plunger shaft 32 remains in the static position does not impede the exit of fluids from the barrel chamber 9. The sealing cap 102 should be returned to the plunger shaft when a recovery operations is completed.

In full fluid recovery operations (when extracting fluids after completion of injections), it is preferred that reservoir bottle 2 be inverted to position 2a (see FIG. 1b) to prevent the build up of pressure in the reservoir bottle, which could result in fluid being pushed out the bottle vent. Additionally, shown in FIG. 1b, the fluid line to the reservoir bottle passes through a bubble detector 105, such as a Lifeguard ultrasonic air bubble detector from MOOG, Inc. of Stuttgart, Germany). The bubble detector 105 can be tied to a motor control to send a command to shut off the motor 5 when bubbles are detected in the fluid line "Fluid recovery" may also take place during a syringe fill operation. During syringe fill, fluid is extracted from the reservoir bottle 2 by the motor 5 pump 4. As the fluid is used and the level goes down, air will be pulled into the fluid line where the bubble detector 105 can be tied to a motor control and send a command to shut off the motor and prompt the operator to replace the empty bottle with a replacement bottle when bubbles are detected in the fluid line. After a fluid bottle is replaced the motor can be controlled to run in reverse to push the air out of the line between the sensor and the reservoir bottle 2, then back to forward to pull liquid into the line replacing the air, this will insure that there will be no air in the fluid line that could end up in the syringe, causing the incorrect volume to be dispensed.

If a long or intermediate spring is used in the four port embodiment, the above procedure cannot be used without changing the static position of the valve, as in the long and intermediate spring embodiments, the valve plunger blocks the SF port 24. Hence, the addition step of backing out the valve plunger to open the SF port 24 is needed, and can be readily accomplished, for instance by removing the protective cover 52 of the valve body 30 and backing out the set screw or bolt, or if the insert body 33 is threaded into the guide chamber, by partially backing out the insert body 33.

As described, the preferred valve housing includes four ports, positioned in preferred order of top to bottom as follows: the storage empty port (e.g. SE) 26 (uppermost), the discharge port 22 and the storage fill (e.g. SF) port 24 (intermediate), and the input port (lowermost). And for the three port, the preferred order is as follows: the discharge port 22 (uppermost), the storage fill (e.g. SF) port 24 (intermediate), and the input port (lowermost). The order may be reversed if the syringe fills from the top, in which event, the insert body would be located on the bottom of the valve housing. The invention as described has substantially fewer components than the prior art spool valve. To clean the device, the valve plunger mechanisms is easily removed from the valve guide chamber from the top of the syringe, hence the fluid lines do not have to be removed. This eliminates the need to first remove the fluid from the supply line before removal of the valve body for cleaning.

The tension or degree of compression of the biasing member is easily settable without substantial disassembly of the device, and because the valve plunger can be manually set to the fill position, the system can be readily discharged by reversing the motor to draw down fluids stored in the syringe barrel chamber and fluid lines. The valve plunger as shown, moves in a reciprocating linear motion within the guide chamber, and hence, will not lock-up as in the prior art spool valve design. The use of a valve plunger removes the valve insertion location from the fluid supply port path, and streamlines fluid flow through the valve. The valve plunger adds the ability to externally adjust the plunger position setting during syringe operation. The removable plunger assembly can be removed with limited fluid loss or leakage. Finally, the syringe can still be loaded manually by drawing fluids in from the needle by operation of the handles with the syringe in the static position.

The invention claimed is:

1. A syringe system comprising a syringe having a body and a hollow barrel chamber, a plunger shaft slidable in said barrel chamber, a needle body adapted for holding a needle, and a valve body, said valve body having a valve guide chamber, said valve guide chamber having an input port fluidly connectable to a fluid pressurizing means, a storage fill port and a storage empty port in fluid communication with said barrel chamber, and a discharge port in fluid communication with said needle body, a valve plunger linearly slidable in said valve guide chamber, a biasing member coupled to said valve plunger, said valve plunger moveable to a fill position and a discharge position, said fill position wherein said discharge port and storage empty ports are closed by said plunger valve and said input port and said storage fill port are opened, said discharge position wherein said input port and said storage fill port are closed by said plunger valve and said storage empty port and said discharge port are opened, said valve plunger assuming said fill position in response to a positive pressure asserted by the fluid pressurizing means at said input port, said input port and discharge port vertically spaced apart in said valve guide chamber, and said storage fill port and storage discharge port are vertically spaced apart in said valve guide chamber.

2. The syringe system according to claim 1 wherein said valve plunger assumes said discharge position when a negative pressure is exerted at said input port by the fluid pressurizing means.

3. The syringe system according to claim 1 wherein said valve plunger assumes an intermediate position in response to said biasing means when no pressure is exerted at said input port by the fluid pressurizing means, said intermediate position having said discharge, said input, said storage fill port and said storage empty port closed.

4. A syringe system comprising a syringe having a body and a hollow barrel chamber, a plunger shaft slidable in said barrel chamber, a needle body adapted for holding a needle, and a valve housing,
said valve housing having a valve guide chamber therein, said valve guide chamber having an input port fluidly connectable to a fluid pressurizing means, a storage fill port in fluid communication with said barrel chamber, and a discharge port in fluid communication with said needle body,
a valve body, said valve body comprising a valve plunger slidable in said valve guide chamber, and a biasing member coupled to said valve plunger at a first end of said biasing member,
said valve plunger slidable to a fill position and a discharge position in said valve guide chamber, said fill position wherein said discharge port is closed and said input port and said storage fill port are opened, and said discharge position wherein said input port is closed and said storage fill port and said discharge port are opened, said valve plunger assumes said fill position when a positive pressure is asserted at said input port by the fluid pressurizing means,
wherein said valve body further comprises an insert body, said insert body removably positioned in said valve guide chamber, said biasing member supported by said insert member, said valve body further having an adjustment means positioned on said insert body to adjust said fill position of said valve plunger in said valve guide chamber with said insert body positioned in said valve guide chamber.

5. The syringe system of claim 1 wherein said valve body further comprises an insert body, said insert body removably positioned in said valve guide chamber, valve body further having an adjustment means positioned on said insert body to adjust the position of the valve plunger in the valve guide chamber, said adjustment means adjusting said fill position of said valve plunger with said insert body positioned in said valve guide chamber.

6. The syringe system according to claim 4 wherein said input port includes a valve seat, and said valve plunger is adapted to seat against said input port seat when assuming said discharge position.

7. The syringe system according to claim 3 wherein said input port includes a valve seat, and said valve plunger is adapted to seat against said input port seat when assuming said intermediary position.

8. A method of dispensing fluid from a syringe system, said syringe system, comprising:
a syringe having a body and a hollow barrel chamber, a plunger shaft slidable in said barrel chamber, a needle body adapted for holding a needle, and a valve housing, said valve housing having a valve guide chamber therein, said valve guide chamber having an input port fluidly connected to a fluid pressurizing means, said fluid pressuring means connected to a supply of fluid, a storage port in fluid communication with said barrel chamber, and a discharge port in fluid communication with said needle body,
a valve body, said valve body comprising a valve plunger linearly slidable in said valve guide chamber, and a biasing member coupled to said valve plunger at a first end of said biasing member,
said valve plunger slidable to a fill position and discharge position in said valve guide chamber, said fill position wherein said discharge port is closed by said valve plunger and said input port and said storage port are opened, and said discharge position wherein said input port is closed by said valve plunger and said storage port and said discharge port are opened, said valve plunger assumes said fill position when a positive pressure is asserted at said input port by said fluid pressuring means;

said method comprising the steps of (a) activating said fluid pressuring means to provide a positive pressure and pump fluid from said fluid supply to said input port on said syringe until a desired amount of fluid is stored in said barrel chamber; (b) de-activating said fluid pressurizing means; (c) activating said fluid pressurizing means to provide a negative pressure at said input port, (d) de-activating said fluid pressurizing means; (e) sliding said plunger shaft into said barrel chamber to dispense fluid from said barrel chamber to said needle body.

9. A method of recovering fluids from a syringe system, said syringe system, comprising:

a syringe having a body and a hollow barrel chamber, said syringe system further having a closable vent to vent said hollow barrel chamber, a plunger shaft slidable in said barrel chamber, a needle body adapted for holding a needle, and a valve housing, said valve housing having a valve guide chamber therein, said valve guide chamber having an input port fluidly connected to a fluid pressurizing means, said fluid pressuring means connected to a supply of fluid, a storage port in fluid communication with said barrel chamber, and a discharge port in fluid communication with said needle body, a valve body, said valve body comprising a valve plunger linearly slidable in said valve guide chamber, and a biasing member coupled to said valve plunger at a first end of said biasing member, said valve body further comprising an insert body, said insert body removably positioned in said valve guide chamber, said biasing member coupled to said insert member, said valve plunger linearly slidable to a fill position and a discharge position in said valve guide chamber, said fill position wherein said discharge port is closed and said input port and said storage port are opened, and said discharge position wherein said input port is closed and said storage port and said discharge port are opened, said valve plunger assumes said fill position when a positive pressure is asserted at said input port by said fluid pressuring means;

said method comprising the steps of (a) maintaining said valve plunger in said first position, (b) opening said vent (c) activating said fluid pressuring means to supply negative pressure at said input port to thereby withdraw fluids sorted in said barrel chamber through said input port.

10. A method of recovering fluids from a syringe system, said syringe system comprising:

a syringe having a body and a hollow barrel chamber, said syringe system further having a closable vent to vent said hollow barrel chamber, a plunger shaft slidable in said barrel chamber, a needle body adapted for holding a needle, and a valve body, said valve body having a valve guide chamber, said valve guide chamber having an input port fluidly connected to a fluid pressurizing means, a storage fill port and a storage empty port in fluid communication with said barrel chamber, and a discharge port in fluid communication with said needle body, a valve plunger linearly slidable in said valve guide chamber, a biasing member coupled to said valve plunger, said valve plunger moveable to a fill position and a discharge position, said fill position wherein said discharge port and storage empty ports are closed and said input port and said storage fill port are opened, said discharge position wherein said input port and said storage fill port are closed and said storage empty port and said discharge port are opened, said valve plunger assuming said fill position in response to a positive pressure asserted by said fluid pressurizing means at said input port; said valve plunger assuming said discharge position when said fluid pressurizing means asserts no pressure at said input port;

said method comprising the steps of (a) opening said vent (b) activating said fluid pressurizing means to supply negative pressure at said input port to thereby withdraw fluids sorted in said barrel chamber through said input port.

11. The syringe system of claim 1 wherein said syringe further comprises a closable vent to vent said hollow barrel chamber.

12. The syringe system of claim 11 wherein said plunger shaft has a channel therein, and said closable vent comprises a check valve positioned on said plunger shaft channel.

13. The syringe system of claim 1 wherein said fluid pressuring means comprises a pump.

14. The syringe system of claim 4 where said valve plunger assumes an intermediate position in response to said biasing means when no pressure is exerted at said input port by the fluid pressurizing means, said intermediate position having said discharge port, said input port, and said storage fill port closed.

* * * * *